(12) United States Patent
Chiapetta et al.

(10) Patent No.: US 11,471,680 B2
(45) Date of Patent: Oct. 18, 2022

(54) SYSTEMS AND INTERFACES FOR OCULAR THERAPY

(71) Applicant: BIOVISICS MEDICAL, LLC, Delano, MN (US)

(72) Inventors: James R. Chiapetta, Delano, MN (US); Paul Rockley, Corona Del Mar, CA (US)

(73) Assignee: Biovisics, Inc., Delano, MN (US)

( * ) Notice: Subject to any disclaimer, the term of this patent is extended or adjusted under 35 U.S.C. 154(b) by 9 days.

(21) Appl. No.: 16/844,421

(22) Filed: Apr. 9, 2020

(65) Prior Publication Data

US 2020/0324114 A1 Oct. 15, 2020

Related U.S. Application Data

(60) Provisional application No. 62/832,134, filed on Apr. 10, 2019.

(51) Int. Cl.
| | | |
|---|---|---|
| *A61N 1/36* | (2006.01) | |
| *A61N 1/04* | (2006.01) | |
| *A61N 1/08* | (2006.01) | |
| *A61N 1/37* | (2006.01) | |
| *A61N 1/372* | (2006.01) | |

(52) U.S. Cl.
CPC ....... *A61N 1/36046* (2013.01); *A61N 1/0472* (2013.01); *A61N 1/08* (2013.01); *A61N 1/37282* (2013.01); *A61N 2001/083* (2013.01)

(58) Field of Classification Search
CPC .. A61N 1/0408; A61N 1/0472; A61N 1/0484; A61N 1/08; A61N 1/37282; A61N 1/36046; A61N 2001/083; A61M 2021/0044
See application file for complete search history.

(56) References Cited

U.S. PATENT DOCUMENTS

| | | | |
|---|---|---|---|
| 2,283,752 A | 5/1942 | Gonsett | |
| 2,527,947 A | 10/1950 | Loos | |

(Continued)

FOREIGN PATENT DOCUMENTS

| | | |
|---|---|---|
| CN | 1096460 A | 12/1994 |
| DE | 202012003100 U1 | 10/2012 |

(Continued)

OTHER PUBLICATIONS

International Search Report and Written Opinion dated Jul. 10, 2020 for International Application No. PCT/US2020/027438.

(Continued)

*Primary Examiner* — Carl H Layno
*Assistant Examiner* — Anh-Khoa N Dinh
(74) *Attorney, Agent, or Firm* — Seager, Tufte & Wickhem, LLP

(57) ABSTRACT

Methods, systems and apparatuses for delivering electrical or other therapy in the vicinity of the eye, comprising eyepieces having a plurality of electrodes that are placed on the eyelid. Some examples are just eyepieces having a periphery that partly surrounds the eye, other examples fully surround the eye or include a temporal portion configured to extend to the temple of the user. Some examples also include a field that covers the eye to take the form of a goggle. Numerous configurations for power supply and therapy output are discussed.

20 Claims, 25 Drawing Sheets

(56) References Cited

U.S. PATENT DOCUMENTS

| | | |
|---|---|---|
| 2,760,483 A | 8/1956 | Tassicker |
| 3,376,870 A | 4/1968 | Yamamoto et al. |
| 3,669,119 A | 6/1972 | Symmes |
| D246,529 S | 11/1977 | Willard |
| 4,162,542 A | 7/1979 | Frank |
| D280,670 S | 9/1985 | Fireman |
| 4,551,149 A | 11/1985 | Scairra |
| 4,614,193 A | 9/1986 | Liss et al. |
| 4,628,933 A | 12/1986 | Michelson |
| 4,664,117 A | 5/1987 | Beck |
| 4,712,558 A | 12/1987 | Kidd et al. |
| 4,979,811 A | 12/1990 | Boyer |
| 5,024,223 A | 6/1991 | Chow |
| 5,099,829 A * | 3/1992 | Wu .................... A61H 39/002 128/907 |
| 5,109,844 A | 5/1992 | De Juan et al. |
| 5,147,284 A | 9/1992 | Fedorov et al. |
| 5,154,174 A | 10/1992 | Hawlina |
| 5,193,540 A | 3/1993 | Schulman et al. |
| 5,263,200 A | 11/1993 | Miller |
| 5,522,864 A | 6/1996 | Wallace et al. |
| 5,556,423 A | 9/1996 | Chow et al. |
| 5,597,381 A | 1/1997 | Rizzo, III |
| 5,643,330 A | 7/1997 | Holsheimer et al. |
| 5,782,894 A * | 7/1998 | Israel ................ A61N 1/36046 607/53 |
| 5,836,996 A | 11/1998 | Doorish |
| 5,843,147 A | 12/1998 | Testerman et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 6,007,532 A | 12/1999 | Netherly |
| D421,124 S | 2/2000 | Yavitz |
| 6,035,236 A | 3/2000 | Jarding et al. |
| D425,623 S | 5/2000 | Funk |
| D429,817 S | 8/2000 | Banks |
| 6,101,411 A | 8/2000 | Newsome |
| 6,131,208 A | 10/2000 | Banks |
| 6,154,671 A | 11/2000 | Parel et al. |
| D440,660 S | 4/2001 | Sternberg |
| 6,230,057 B1 | 5/2001 | Chow et al. |
| D444,561 S | 7/2001 | Stein |
| 6,275,735 B1 | 8/2001 | Jarding et al. |
| 6,282,449 B1 | 8/2001 | Kamerling et al. |
| 6,306,075 B1 | 10/2001 | Shadduck |
| 6,324,429 B1 | 11/2001 | Shire et al. |
| 6,389,317 B1 | 5/2002 | Chow et al. |
| 6,400,989 B1 | 6/2002 | Eckmiller |
| 6,408,211 B1 | 6/2002 | Powell |
| 6,424,864 B1 | 7/2002 | Matsuura |
| 6,442,431 B1 | 8/2002 | Veraart et al. |
| 6,458,157 B1 | 10/2002 | Suaning |
| 6,515,227 B1 | 2/2003 | Massey et al. |
| 6,611,716 B2 | 8/2003 | Chow et al. |
| 6,755,530 B1 | 6/2004 | Loftus et al. |
| 6,792,314 B2 | 9/2004 | Byers et al. |
| 6,976,998 B2 | 12/2005 | Rizzo et al. |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,031,776 B2 | 4/2006 | Chow et al. |
| 7,037,943 B2 | 5/2006 | Peyman |
| 7,043,308 B2 | 5/2006 | Cohen |
| 7,047,080 B2 | 5/2006 | Palanker et al. |
| 7,058,455 B2 | 6/2006 | Huie, Jr. et al. |
| 7,067,327 B2 | 6/2006 | Wu et al. |
| 7,130,693 B1 | 10/2006 | Montalbo |
| 7,139,612 B2 | 11/2006 | Chow et al. |
| 7,146,209 B2 | 12/2006 | Gross et al. |
| 7,147,865 B2 | 12/2006 | Fishman et al. |
| 7,158,834 B2 | 1/2007 | Paul, Jr. |
| 7,158,836 B2 | 1/2007 | Suzuki |
| 7,248,928 B2 | 7/2007 | Yagi |
| 7,251,528 B2 | 7/2007 | Harold |
| 7,306,621 B1 | 12/2007 | Halla et al. |
| 7,321,796 B2 | 1/2008 | Fink et al. |
| 7,337,008 B2 | 2/2008 | Terasawa et al. |
| 7,398,124 B2 | 7/2008 | Fujikado et al. |
| 7,400,021 B2 | 7/2008 | Wu et al. |
| 7,447,547 B2 | 11/2008 | Palanker |
| 7,447,548 B2 | 11/2008 | Eckmiller |
| 7,458,456 B2 | 12/2008 | Hogan et al. |
| 7,556,621 B2 | 7/2009 | Palanker et al. |
| 7,877,148 B2 | 1/2011 | Chowdhury et al. |
| 7,883,535 B2 | 2/2011 | Cantin et al. |
| 7,974,699 B2 | 7/2011 | Tano et al. |
| 7,979,134 B2 | 7/2011 | Chow et al. |
| 7,981,062 B2 | 7/2011 | Chow et al. |
| 8,000,804 B1 | 8/2011 | Wessendorf et al. |
| 8,039,445 B2 | 10/2011 | Behar-Cohen et al. |
| 8,070,688 B2 | 12/2011 | Livne et al. |
| 8,190,266 B2 | 5/2012 | Ameri et al. |
| 8,197,539 B2 | 6/2012 | Nasiatka et al. |
| 8,260,428 B2 | 9/2012 | Fink et al. |
| 8,265,764 B2 | 9/2012 | Fano et al. |
| 8,306,626 B2 | 11/2012 | Chow et al. |
| 8,377,120 B2 | 2/2013 | Lipshitz et al. |
| 8,396,561 B2 | 3/2013 | Pezaris et al. |
| 8,396,562 B2 | 3/2013 | Ameri et al. |
| 8,398,692 B2 | 3/2013 | Deisseroth et al. |
| 8,433,417 B2 | 4/2013 | Flood |
| 8,478,415 B1 | 7/2013 | Halla et al. |
| 8,515,548 B2 | 8/2013 | Rofougaran et al. |
| 8,612,002 B2 | 12/2013 | Faltys et al. |
| 8,634,923 B2 | 1/2014 | Sharpee et al. |
| 8,639,345 B2 | 1/2014 | Eipper et al. |
| 8,691,877 B2 | 4/2014 | Yun et al. |
| 8,700,167 B2 | 4/2014 | Sabel |
| 8,725,266 B2 | 5/2014 | Olson et al. |
| 8,731,683 B2 | 5/2014 | Lindenthaler |
| 8,734,513 B2 | 5/2014 | Wu et al. |
| 8,771,349 B2 | 7/2014 | Schachar |
| 8,788,041 B2 | 7/2014 | Yun et al. |
| 8,801,942 B2 | 8/2014 | Scorsone et al. |
| 8,824,156 B2 | 9/2014 | Tai et al. |
| 8,852,290 B2 | 10/2014 | Rowley et al. |
| 8,864,805 B2 | 10/2014 | Deisseroth et al. |
| 8,868,202 B2 | 10/2014 | Della Santina et al. |
| 8,903,495 B2 | 12/2014 | Greenberg et al. |
| 8,909,340 B2 | 12/2014 | Yun |
| 8,918,186 B2 | 12/2014 | Tiedtke |
| 8,918,188 B2 | 12/2014 | Tiedtke |
| 8,972,004 B2 | 3/2015 | Simon et al. |
| 9,002,463 B2 | 4/2015 | Tiedtke |
| 9,037,251 B2 | 5/2015 | Narayan et al. |
| 9,037,252 B2 | 5/2015 | Tiedtke |
| 9,037,255 B2 | 5/2015 | Rocke et al. |
| 9,078,743 B2 | 7/2015 | Tai et al. |
| 9,079,042 B2 | 7/2015 | Tiedtke et al. |
| 9,125,734 B2 | 9/2015 | Keller et al. |
| 9,144,608 B2 | 9/2015 | Olson et al. |
| 9,162,060 B2 | 10/2015 | Wrobel et al. |
| 9,162,061 B2 | 10/2015 | Barnes |
| 9,180,309 B2 | 11/2015 | Nirenberg et al. |
| 9,186,523 B1 | 11/2015 | Zolli |
| 9,187,745 B2 | 11/2015 | Deisseroth et al. |
| 9,199,080 B2 | 12/2015 | Gekeler et al. |
| 9,220,634 B2 | 12/2015 | Nirenberg |
| 9,220,894 B1 | 12/2015 | Zhu |
| 9,233,026 B2 | 1/2016 | Ziemeck et al. |
| 9,233,258 B2 | 1/2016 | Simon et al. |
| 9,242,067 B2 | 1/2016 | Shore et al. |
| 9,403,001 B2 | 1/2016 | Simon et al. |
| 9,302,103 B1 | 4/2016 | Nirenberg |
| 9,322,713 B2 | 4/2016 | Narayan et al. |
| 9,326,887 B2 | 5/2016 | Yun |
| 9,339,650 B2 | 5/2016 | Rezai et al. |
| 9,345,568 B2 | 5/2016 | Cho et al. |
| 9,370,348 B2 | 6/2016 | Tally et al. |
| 9,381,355 B2 | 7/2016 | Khraiche et al. |
| 9,452,289 B2 | 9/2016 | Chichilnisky et al. |

(56) References Cited

U.S. PATENT DOCUMENTS

| | | | |
|---|---|---|---|
| 9,456,836 B2 | 10/2016 | Boling et al. |
| 9,468,760 B1 | 10/2016 | Lin |
| 9,498,380 B2 | 11/2016 | Berdahl et al. |
| 9,630,013 B2 | 4/2017 | Bachinski et al. |
| 9,636,212 B2 | 5/2017 | Tiedtke et al. |
| 9,682,232 B2 | 6/2017 | Shore et al. |
| 9,687,652 B2 | 6/2017 | Franke et al. |
| 9,697,746 B2 | 7/2017 | Barnes et al. |
| 9,737,710 B2 | 8/2017 | Fan |
| 9,737,711 B2 | 8/2017 | Twyford et al. |
| 9,789,312 B2 | 10/2017 | Fukuma et al. |
| 9,795,787 B2 | 10/2017 | Cho et al. |
| 9,821,003 B2 | 11/2017 | Yun |
| 9,821,159 B2 | 11/2017 | Ackermann et al. |
| 9,844,459 B2 | 12/2017 | Badawi |
| 9,867,988 B2 | 1/2018 | Fink et al. |
| 9,884,180 B1 | 2/2018 | Ho et al. |
| 9,895,529 B2 | 2/2018 | Tiedtke |
| 9,925,373 B2 | 3/2018 | Nirenberg |
| 9,931,506 B2 | 4/2018 | Chung et al. |
| 9,937,346 B2 | 4/2018 | Lineaweaver et al. |
| 9,950,153 B2 | 4/2018 | Wagner et al. |
| 9,956,425 B2 | 5/2018 | Peyman |
| 9,962,540 B2 | 5/2018 | Picaud et al. |
| 9,962,558 B2 | 5/2018 | Peyman |
| 9,980,388 B2 | 5/2018 | Tai et al. |
| 9,990,861 B2 | 6/2018 | Chichilnisky et al. |
| 10,010,364 B2 | 7/2018 | Harrington |
| 10,071,251 B2 | 9/2018 | Bachinski et al. |
| 10,112,048 B2 | 10/2018 | Franke et al. |
| 10,129,647 B2 | 11/2018 | Seo et al. |
| 10,347,050 B1 | 7/2019 | Wang et al. |
| 2003/0158588 A1 | 8/2003 | Rizzo et al. |
| 2003/0176898 A1* | 9/2003 | Gross ............... A61M 5/1723 607/54 |
| 2003/0233135 A1 | 12/2003 | Yee |
| 2003/0233137 A1 | 12/2003 | Paul, Jr. |
| 2004/0106965 A1 | 6/2004 | Chow |
| 2004/0176820 A1 | 9/2004 | Paul, Jr. |
| 2005/0004625 A1 | 1/2005 | Chow |
| 2005/0049578 A1 | 3/2005 | Tu et al. |
| 2005/0137649 A1 | 6/2005 | Paul, Jr. |
| 2006/0142818 A1 | 6/2006 | Chow et al. |
| 2007/0093877 A1 | 4/2007 | Beecham et al. |
| 2007/0179564 A1 | 8/2007 | Harold |
| 2008/0171929 A1 | 7/2008 | Katims |
| 2008/0194531 A1 | 8/2008 | Steer et al. |
| 2009/0217938 A1 | 9/2009 | Rabe et al. |
| 2009/0287276 A1 | 11/2009 | Greenberg et al. |
| 2011/0081333 A1 | 4/2011 | Shantha et al. |
| 2012/0123501 A1 | 5/2012 | Greenberg et al. |
| 2013/0053733 A1 | 2/2013 | Korb et al. |
| 2013/0066396 A1 | 3/2013 | Gekeler et al. |
| 2013/0184782 A1 | 7/2013 | Eipper et al. |
| 2014/0257433 A1 | 9/2014 | Ackermann et al. |
| 2014/0277435 A1 | 9/2014 | Gefen |
| 2014/0324147 A1 | 10/2014 | Wagner |
| 2015/0018927 A1* | 1/2015 | Warschewske ...... A61N 1/0456 607/141 |
| 2015/0039067 A1 | 2/2015 | Greenberg et al. |
| 2015/0209174 A1 | 7/2015 | Abreu |
| 2016/0051439 A1 | 2/2016 | Brown et al. |
| 2016/0317474 A1 | 11/2016 | Aung et al. |
| 2017/0266445 A1 | 9/2017 | O'Clock |
| 2018/0064935 A1 | 3/2018 | Leonhardt et al. |
| 2018/0228237 A1 | 8/2018 | Zhang et al. |
| 2018/0318585 A1 | 11/2018 | Pfeifer |
| 2018/0318586 A1 | 11/2018 | Salazar |
| 2019/0143116 A1 | 5/2019 | Mowrey |

FOREIGN PATENT DOCUMENTS

| | | | |
|---|---|---|---|
| EP | 1985332 A1 | 10/2008 | |
| GB | 2246709 A | 2/1992 | |
| WO | 2006086452 A1 | 8/2006 | |
| WO | 2013124141 A1 | 8/2013 | |
| WO | 2015095257 A2 | 6/2015 | |
| WO | 2016089751 A1 | 6/2016 | |
| WO | 2017048731 A1 | 3/2017 | |
| WO | WO-2017048731 A1 * | 3/2017 | ......... A61N 1/36031 |
| WO | 2017064500 A1 | 4/2017 | |
| WO | 2018013835 A1 | 1/2018 | |
| WO | 2018129351 A1 | 7/2018 | |
| WO | 2018208009 A1 | 11/2018 | |

OTHER PUBLICATIONS

Chlaihawi et al; "Development of Printed and Flexible Dry ECG Electrodes", Sensing and Bio-Sensing Research, vol. 20, pp. 9-15, 2018.

2019 World Congress Eye and Chip Speaker Abstracts, pp. 20-54, 2019.

Gall et al; Alternating Current Stimulation for Vision Restoration after Optic Nerve Damage: A Randomized Clinical Trial, PLOS One, pp. 1-13, 2016, accessed Nov. 12, 2018.

Chow et al; "The Artificial Silicon Retina in Retinitis Pigmentosa Patients", Trans Am Ophthalmol Soc., vol. 108, pp. 120-154, 2010.

Dawson et al; "Improved Electrode for Electroretinography," Invest. Ophthalmol. Visual Sci. vol. 8, No. 9, pp. 988-991, Sep. 1979, accessed on May 2, 2019.

Diagnosys DTL Brochure, Diagnosys, LLC, 2016, Accessed Nov. 20, 2017.

DTL Installation, Diagnosys LLC, Accessed Oct. 6, 2020.

Bittner et al; "Longevity of Visual Improvements following Transcorneal Electrical Stimulation and Efficacy of Retreatment in Three Individuals with Retinitis Pigmentosa", Graefe's Archive for Clinical and Experimental Ophthalmology, 2017, Published online on Dec. 8, 2017.

H110002B Summary of Safety and Probable Benefits, Second Sight Medical Products Inc., issued Dec. 11, 2001.

H110002C Second Sight Manuals, Second Sight Medical Products Inc., 2013.

Naycheva et al; Phosphene Thresholds Elicited by Trasncorneal Electrical Stimulation in Healthy Subjects and Patients with Retinal Disease, Investigative Ophthalmology and Visual Science, vol. 53, No. 12, pp. 7440-7448, 2012, accessed on Sep. 20, 2018.

Schatz et al; "Transcorneal Electrical Stimulation for Patients with Retinitis Pigmentosa: A Prospective Randomized, Sham-Controlled Follow-Up Study Over 1 Year", Investigative Ophthalmology and Visual Science, vol. 58, No. 1, pp. 257-269, 2017. Accessed on Sep. 25, 2018.

Scyfix SF700 Manual, Instructions for Use, pp. 1-28, Scyfix LLC.

Stauffer et al; "Skin Conformal Polymer Electrodes for Clinical ECG and EEG Recordings," Advanced Healthcare Materials pp. 1-10, 2018.

Manthey et al; "Using Electrical Stimulation to Enhance the Efficacy of Cell Transplantation Therapies for Neurodegenerative Retinal Diseases: Concepts, Challenges, and Future Perspectives", Cell Transplantation, vol. 26, pp. 949-965, 2017.

Invitation To Pay Additional Fees dated Dec. 17, 2019 for International Application No. PCT/US2019/054028.

Invitation To Pay Additional Fees dated Feb. 14, 2020 for International Application No. PCT/US2019/063580.

Invitation To Pay Additional Fees dated Aug. 31, 2020 for International Application No. PCT/US2020/037458.

\* cited by examiner

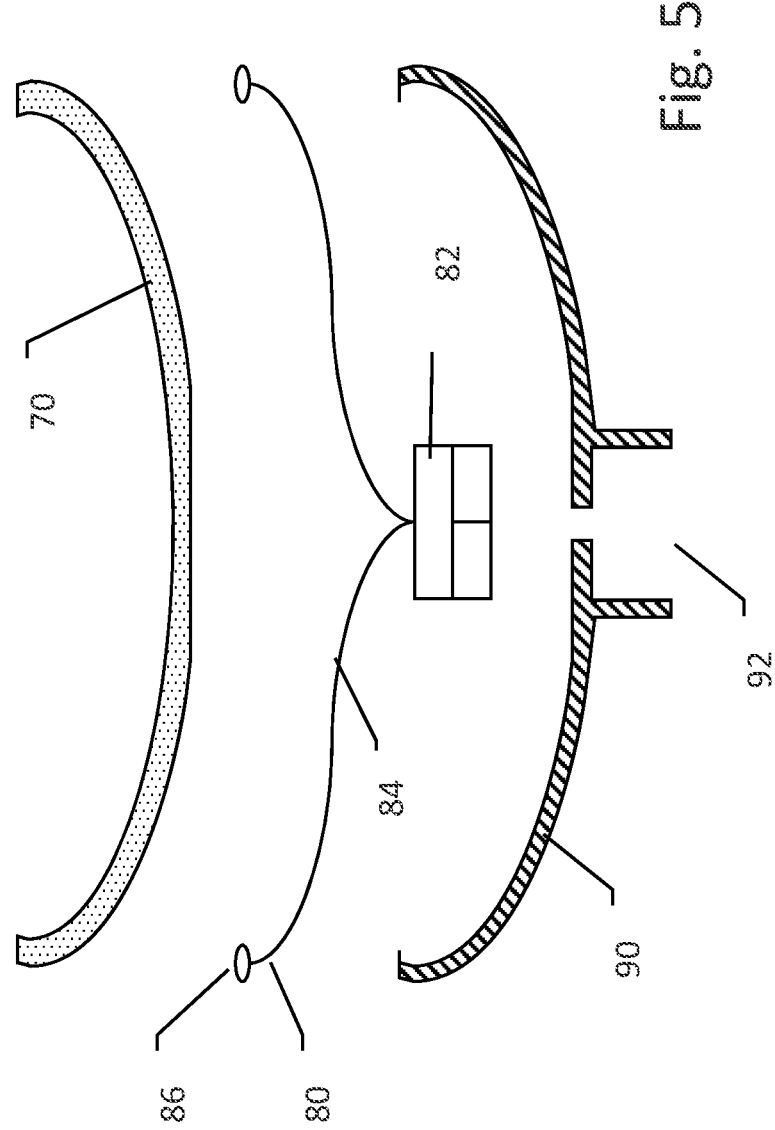

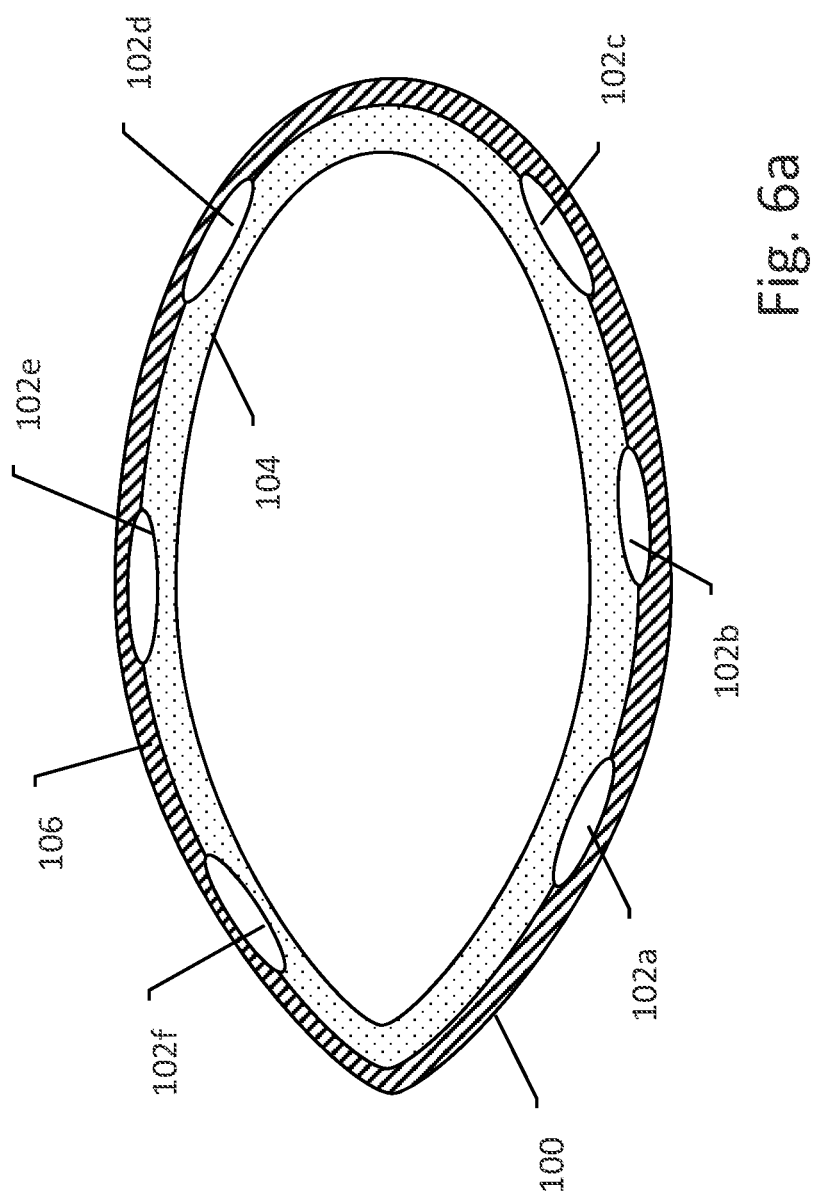

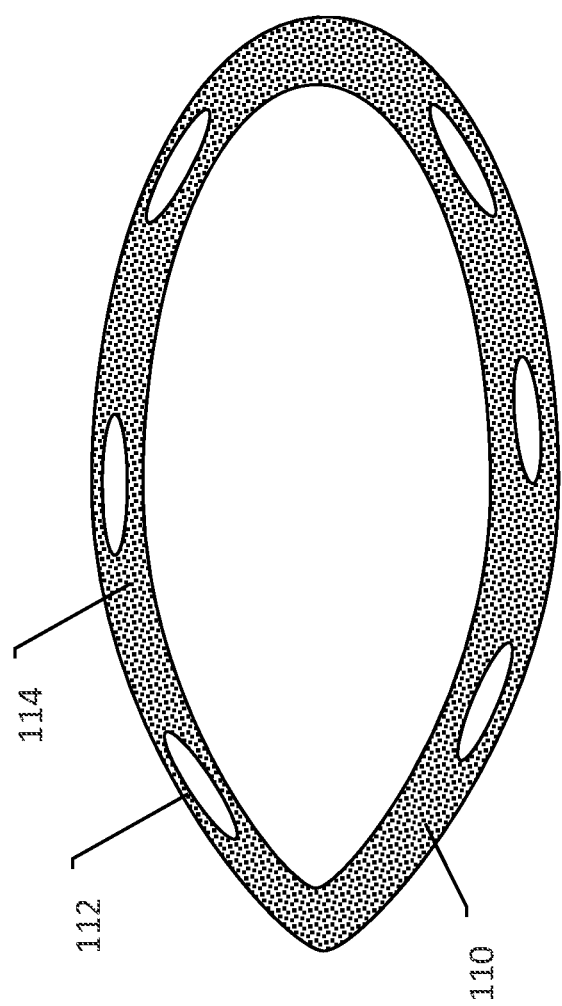

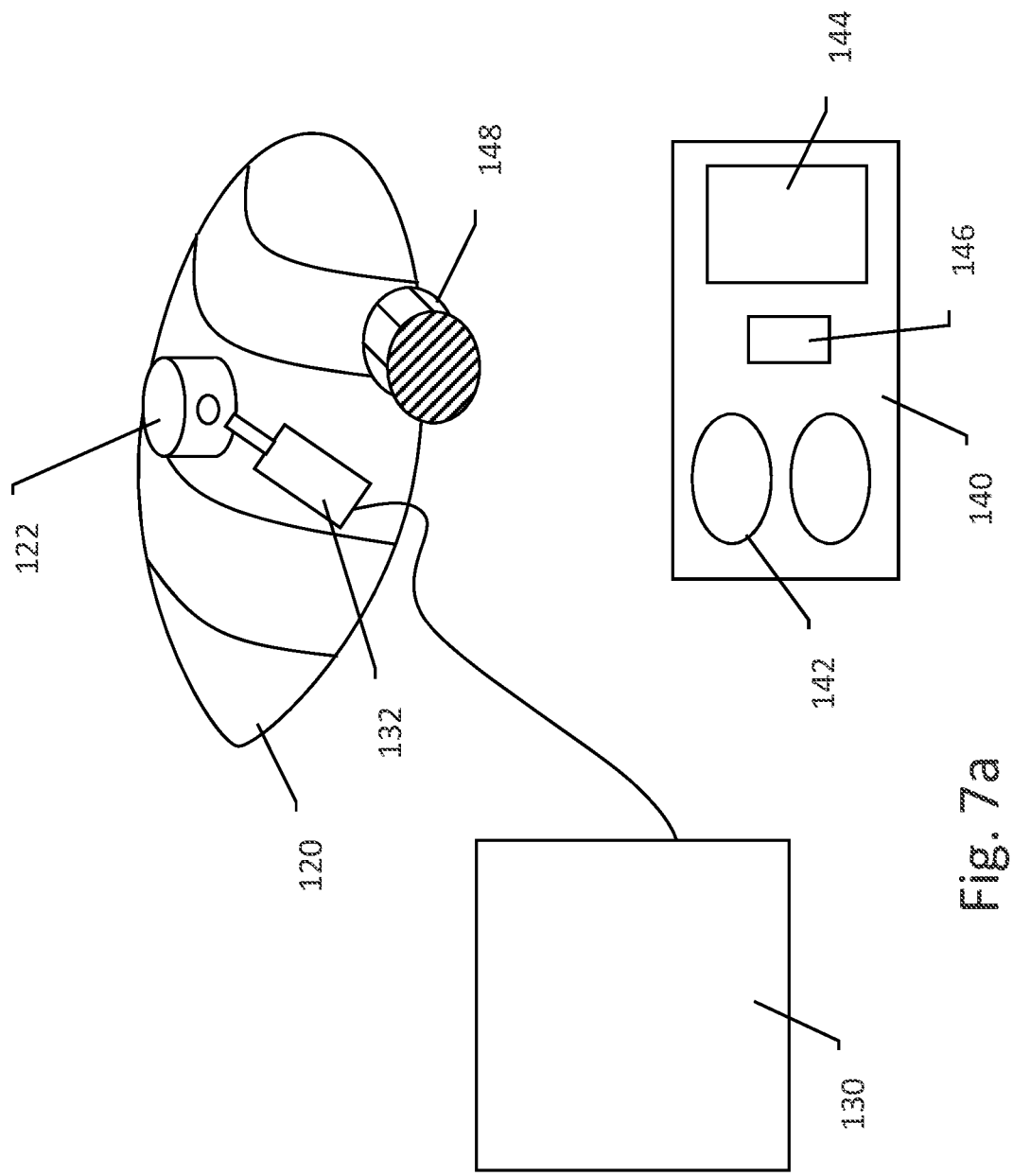

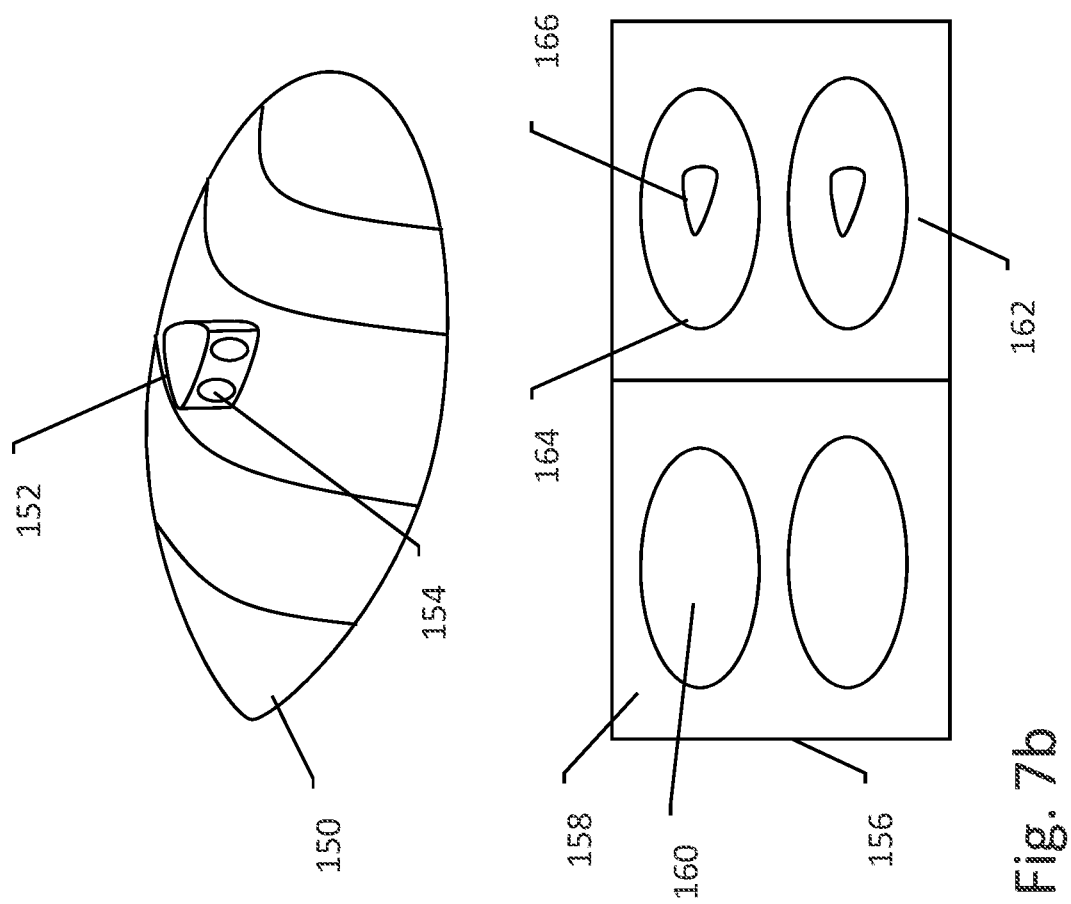

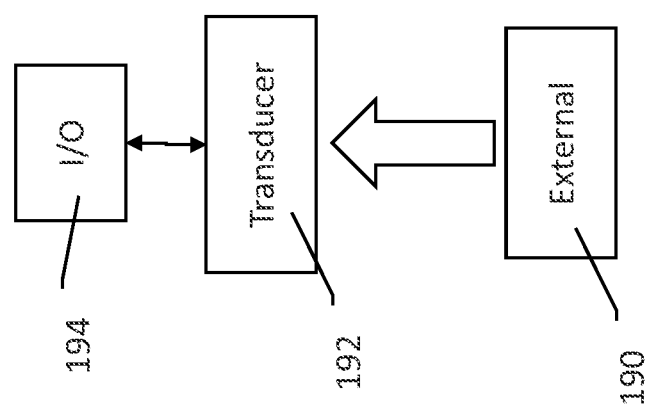

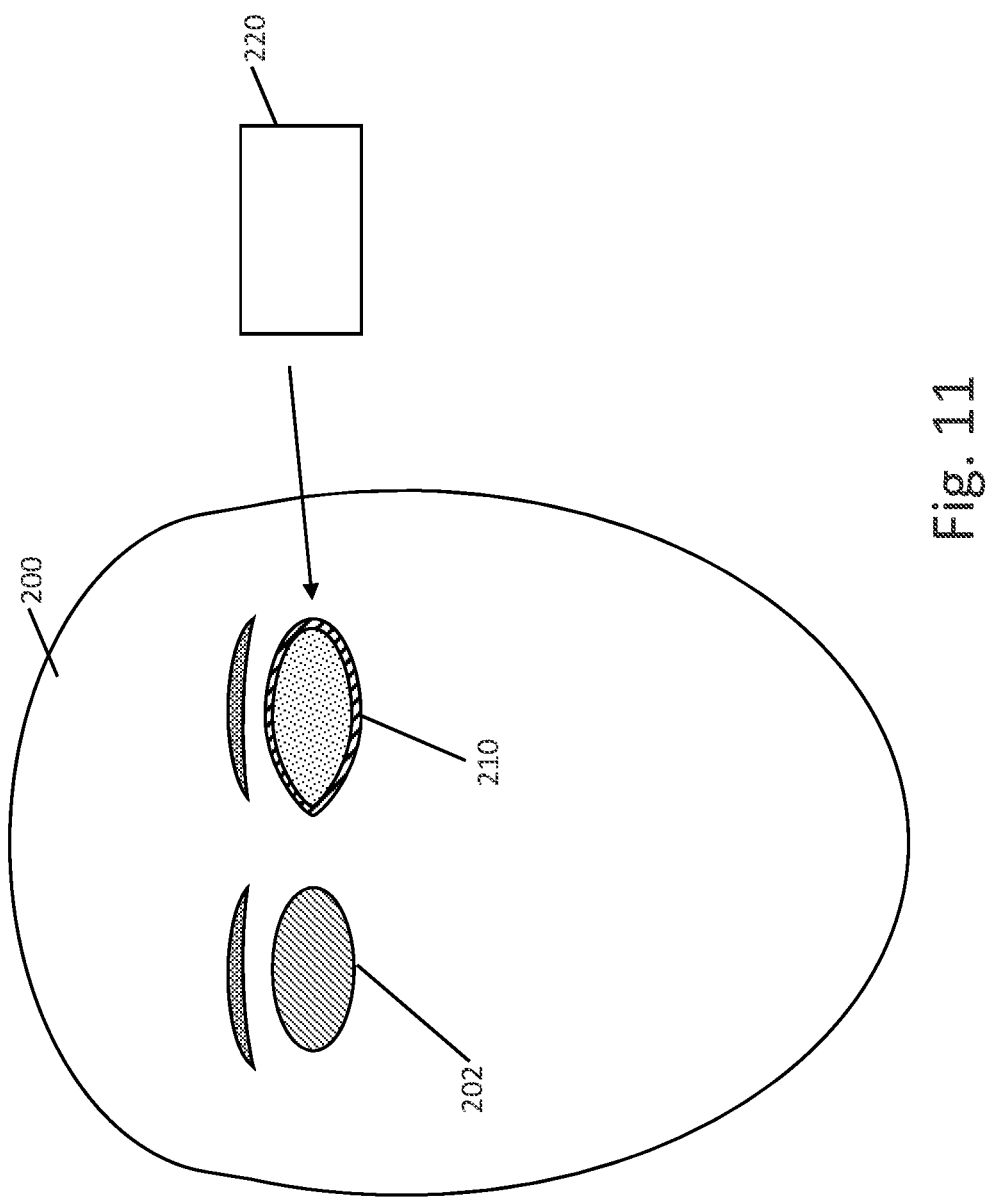

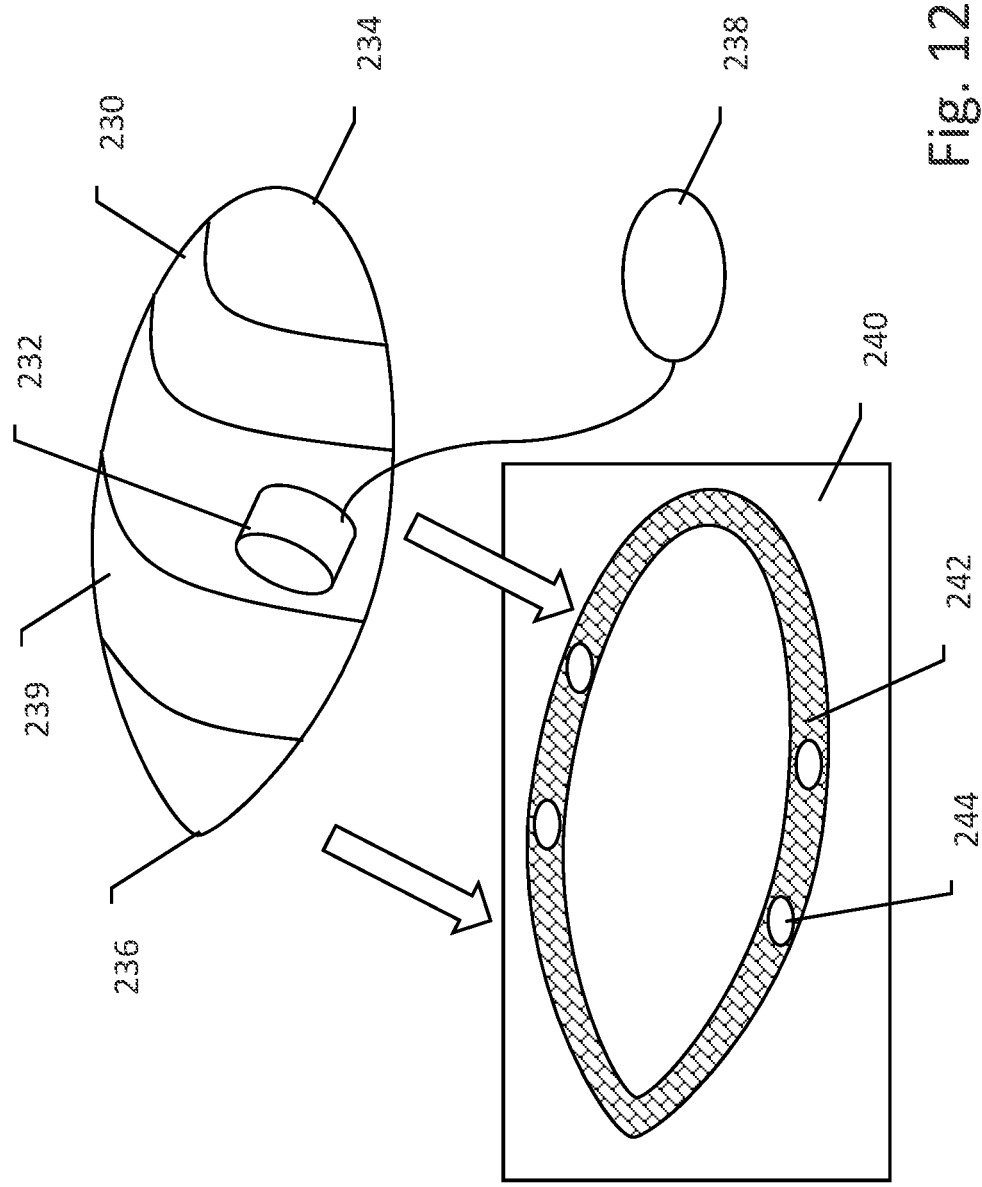

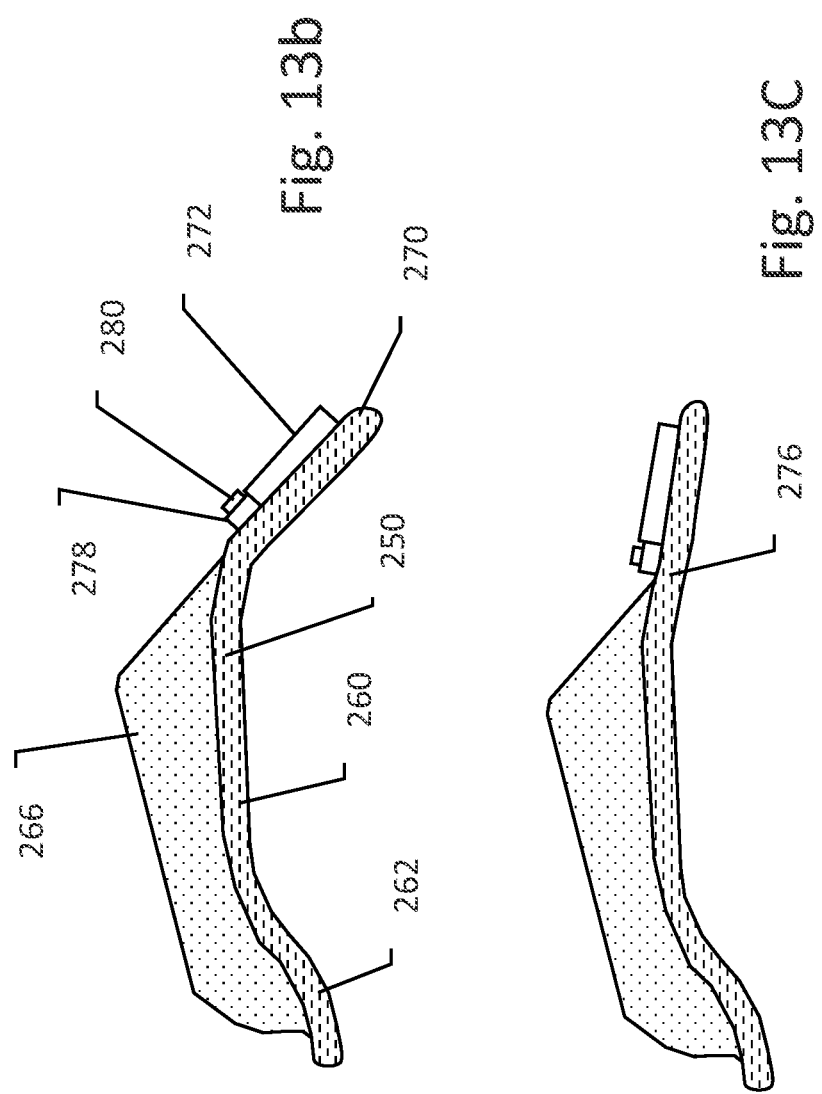

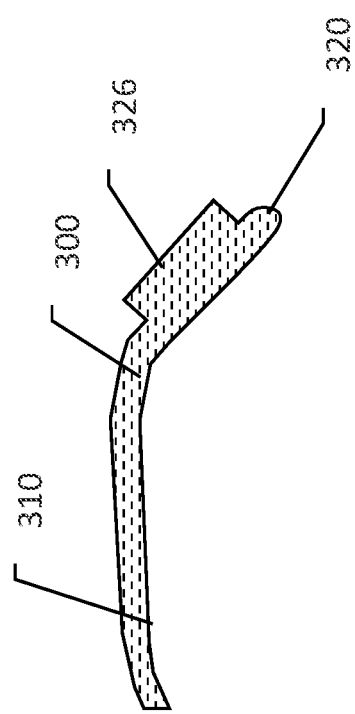
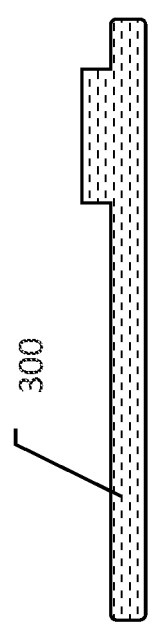

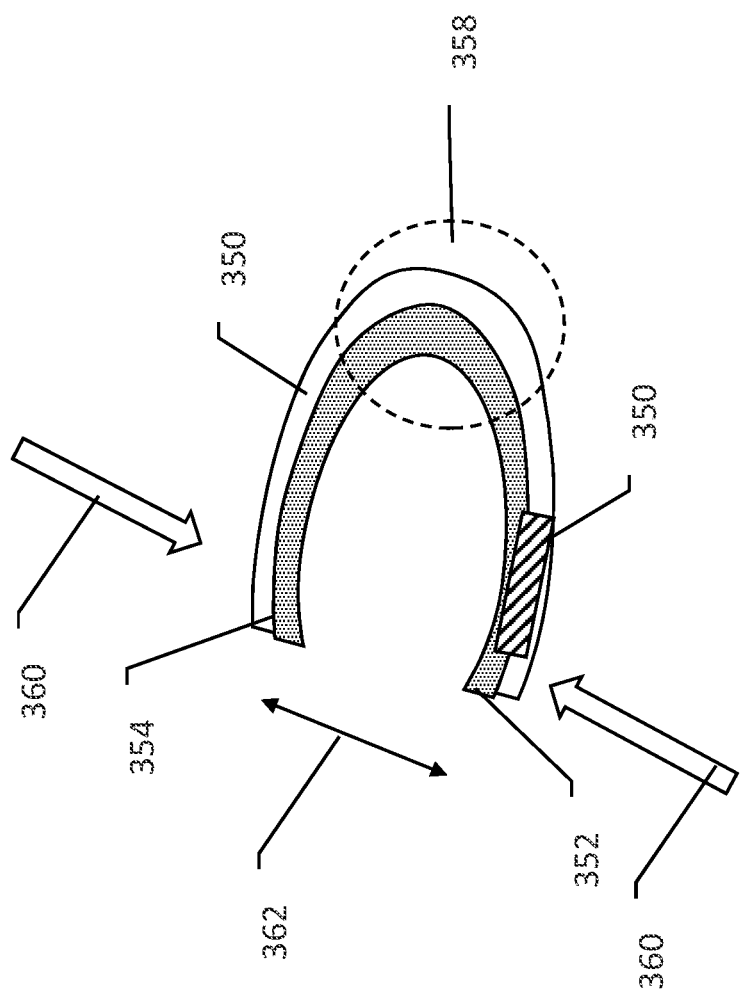

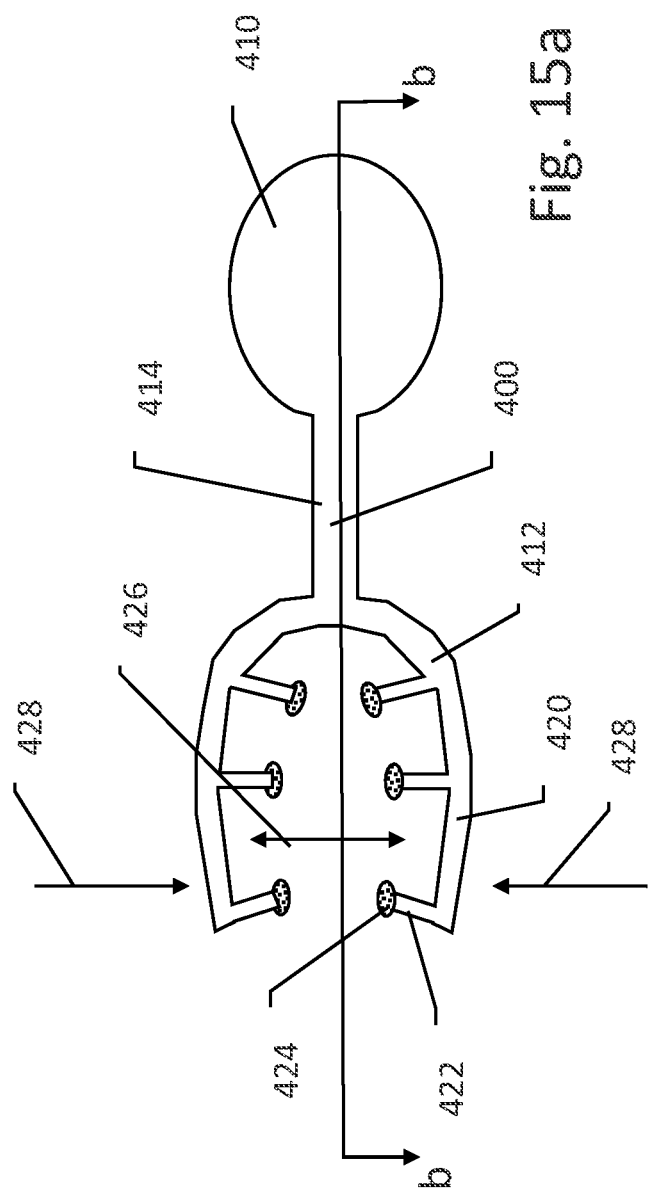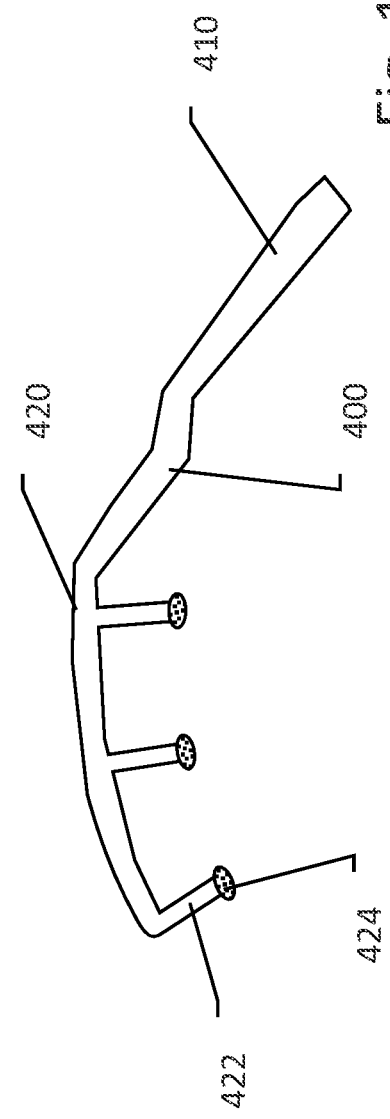

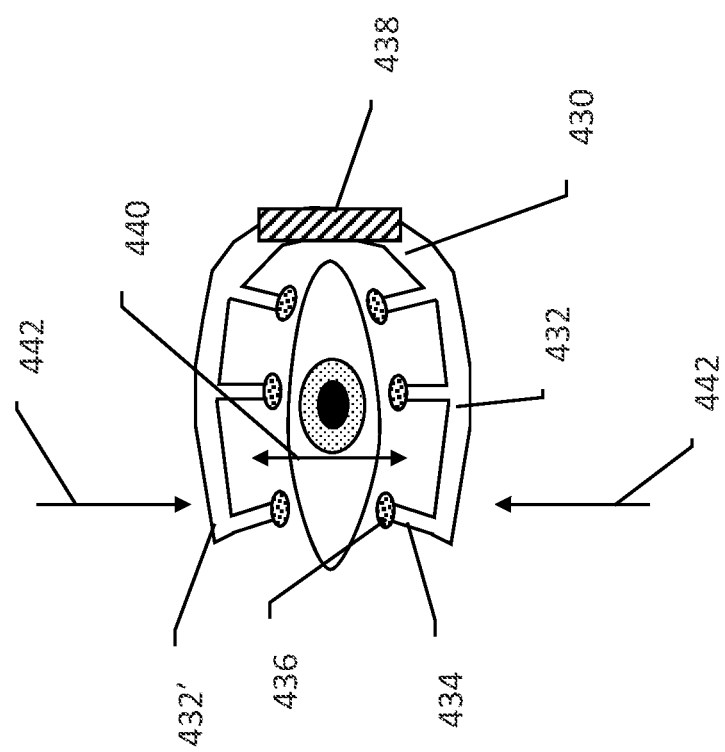

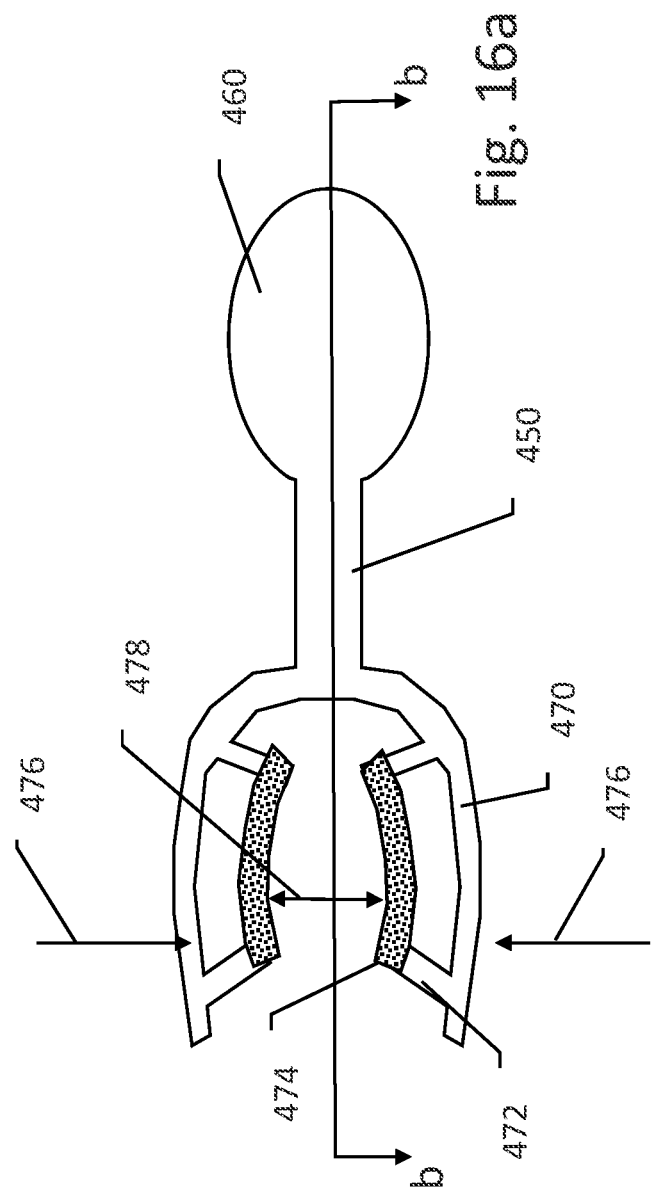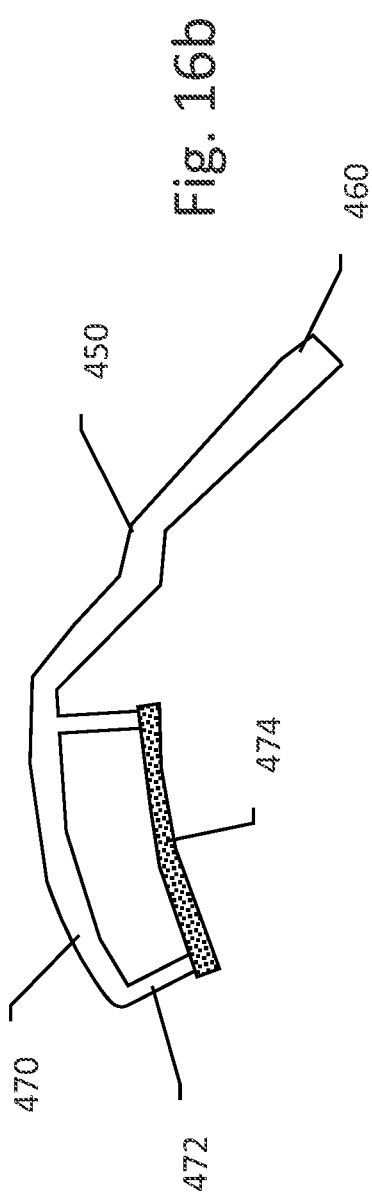

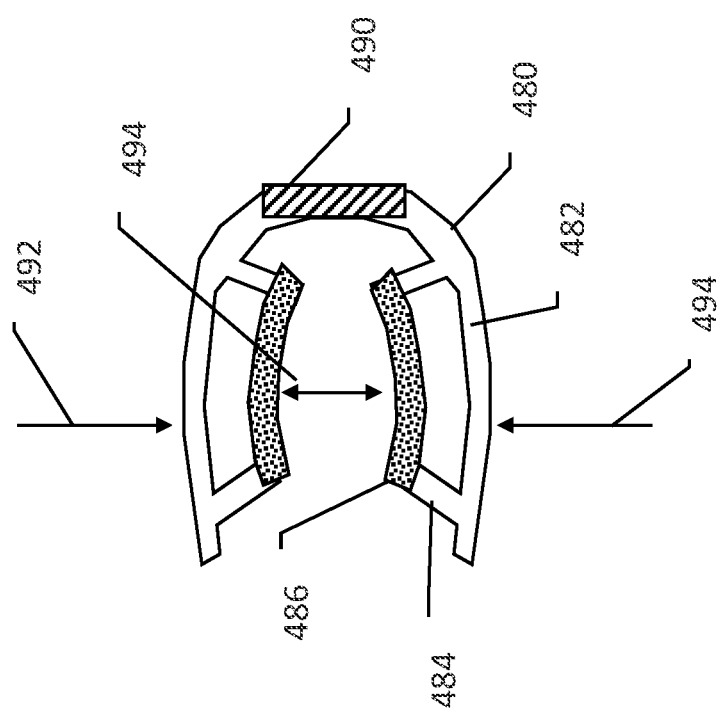

SYSTEMS AND INTERFACES FOR OCULAR THERAPY

CROSS REFERENCE TO RELATED APPLICATIONS

The present application claims the benefit of and priority to U.S. Provisional Patent Application No. 62/832,134, filed on Apr. 10, 2019, and titled SYSTEMS AND INTERFACES FOR OCULAR THERAPY, the disclosure of which is incorporated herein by reference.

FIELD

The present invention relates generally to the field of delivery of therapeutic energy for treatment of various conditions. More particularly, the present invention is directed to systems and methods adapted to deliver energy to the eye and/or surrounding tissue.

BACKGROUND

Therapy to prevent, slow progression of, or reverse diseases of the eye is of great interest. As life expectancy expands, more and more of the population is at risk for age related macular degeneration (AMD). Meanwhile, smaller populations of patients suffer from a variety of maladies, including inherited diseases such as Stargardt's disease, Retinitis Pigmentosa, and other degenerative conditions that affect the retina of the eye. A wide variety of other vision disorders exist which can lead to partial or total blindness. There is a continuing demand for new, adjunctive, and/or alternative systems and methods to treat such disorders including by preventing, arresting or reversing disease progress, or at least by alleviating ongoing symptoms.

A variety of proposed head worn apparatuses have been disclosed for the delivery of electrical stimulus (sometimes referred to as microcurrent therapy) to the eye. Patches, goggles, and devices resembling glasses have been proposed. However, there remains a continuing demand for improved head worn apparatuses for delivering therapy to persons afflicted with diseases of the eye, as well as other conditions (headaches, sleep disorders, fatigue) that may be treated by delivering therapy to the eye and/or surrounding tissue.

OVERVIEW

The present inventors have recognized, among other things, that a problem to be solved is the need for new patient interfaces for delivering energy and/or therapy to the eye and surrounding tissues. One form of energy delivery is electrical therapy which, when applied to the eye may be referred to as "ocular modulation." Such therapy may be electrocurrent therapy, microcurrent therapy or millicurrent therapy, without intending to limit the scope of the invention to a particular range of current with such terms. Existing apparatuses and the patent arts show various apparatuses having a variety of drawbacks. Some products require a plurality of wires to be managed by the patient or user, who may need to use the product independently and/or outside of the clinical environment. For users suffering from impaired vision, adding the difficulty of managing numerous wires can lead to frustration and eventual non-use of therapy products. Some known apparatuses are heavy and bulky, and prevent the user from comfortably relaxing during use. New devices with less wires and less bulk are desired.

A first illustrative and non-limiting example takes the form of a wearable therapy apparatus for placement about the eye of a user comprising a perimeter region including a tissue interface, the perimeter region having a superior edge, and an inferior edge and at least one electrode; a field region defined within the perimeter region; and an electronics module electrically coupled to the at least one electrode, the electronics module adapted to deliver electrical stimulus to the user through the at least one electrode.

Additionally or alternatively, the perimeter region may include an open side. Additionally or alternatively, the perimeter region may comprise a superior arm and an inferior arm, and at least one of the superior arm and inferior arm is flexible to allow compression thereof in a superior-inferior direction prior to placement about the eye of a user, such that release of the compression provide a mechanical force to the tissue surrounding the user's eye aiding in fixation in a desired position. Additionally or alternatively, the perimeter region may comprise a hinging side opposite the open side, the hinging side adapted to allow the superior arm and inferior arm to be pressed toward one another prior to placement about the eye of a user, such that release of the superior and inferior arms in a desired position provides a mechanical force to the tissue surrounding the user's eye aiding in fixation in a desired position. Additionally or alternatively, the mechanical force to the tissue surrounding the user's eye may be sufficient to hold the apparatus in place without the use of an adhesive. Additionally or alternatively, the apparatus may further comprising an adhesive element sized and shaped for use with at least one of the superior and inferior arms to provide fixation to the skin of the user. Additionally or alternatively, the perimeter region may comprise a shape memory material. Additionally or alternatively, the perimeter region may comprise a spring. Additionally or alternatively, the at least one electrode may comprise a superior electrode on the superior arm, and an inferior electrode on the inferior arm. Additionally or alternatively, the superior arm may comprise a bridge coupled to one or more electrode arms carrying an electrode. Additionally or alternatively, the inferior arm may comprise a bridge coupled to one or more electrode arms carrying an electrode. Additionally or alternatively, the superior arm may comprise a bridge coupled to a strut which holds an electrode carrier having one or more electrodes thereon. Additionally or alternatively, the inferior arm may comprise a bridge coupled to a strut which holds an electrode carrier having one or more electrodes thereon. Additionally or alternatively, the apparatus may comprise a nasal edge opposite the open side.

Additionally or alternatively, the apparatus may comprise a temporal edge opposite the open side. Additionally or alternatively, the apparatus may comprise a temporal portion shaped and sized to extend from the eyepiece to the temple of a user when the eyepiece is placed about the eye of a user. Additionally or alternatively, the electronics module may be carried on the temporal portion. Additionally or alternatively, the temporal portion may comprise a port to receive the electronics module. Additionally or alternatively, the temporal portion may comprise a port for receiving a replaceable battery for providing power to the electronics module. Additionally or alternatively, the temporal portion may comprise a temporal electrode for electrically coupling to the temple.

Additionally or alternatively, the field region may form, define, or include a void.

Additionally or alternatively, the wearable therapy apparatus may comprise a temporal portion connected to the perimeter region and shaped and sized to extend from the perimeter region to the temple of a user when the perimeter region is placed about the eye of a user.

Additionally or alternatively, the perimeter may be closed to completely surround the eye of a user when placed thereabout. Additionally or alternatively, the perimeter region may be flexible to allow compression thereof in a superior-inferior direction prior to placement about the eye of a user, such that release of the compression provide a mechanical force to the tissue surrounding the user's eye aiding in fixation in a desired position. Additionally or alternatively, the perimeter region may comprise a hinge adapted to allow compression thereof prior to placement about the eye of a user, such that release of such compression provides a mechanical force to the tissue surrounding the user's eye thereby aiding in fixation in a desired position. Additionally or alternatively, the mechanical force to the tissue surrounding the user's eye may be sufficient to hold the apparatus in place without the use of an adhesive. Additionally or alternatively, the apparatus may comprise an adhesive element sized and shaped for placement on at least a portion of the perimeter to provide fixation to the skin of the user. Additionally or alternatively, the perimeter region may comprise a shape memory material. Additionally or alternatively, the perimeter region may comprise a spring. Additionally or alternatively, the at least one electrode may comprise a superior electrode and an inferior electrode.

Additionally or alternatively, the field region may comprise a solid member defining an inner perimeter adapted to receive a corrective lens. Additionally or alternatively, the field region may be closed and formed of a transparent or semi-transparent material. Additionally or alternatively, the field region may be flexible in at least a superior/inferior direction to aid in mechanically fixing the apparatus in a desired position about the eye of a user. Additionally or alternatively, the electronics module may be directly coupled to the field region.

Additionally or alternatively, the electronics module may be directly coupled to the perimeter region. Additionally or alternatively, the at least one electrode on the perimeter region may comprise at least a first inferior electrode on the inferior edge and at least a first superior electrode on the superior edge. Additionally or alternatively, the tissue interface may be formed of a soft material. Additionally or alternatively, wherein the soft material may be a gel encapsulated in a layer of polymer. Additionally or alternatively, the soft material may be a foam. Additionally or alternatively, the apparatus may further comprise a module port for receiving the electronics module and electrically coupling the electronics module to the electrodes, such that the electronics module may be separated from the rest of the apparatus.

Additionally or alternatively, the perimeter region may be flexible in at least one direction and has a rest configuration, such that a force applied to the perimeter region changes the shape of the perimeter region from the rest configuration, to facilitate placement about the eye of a user, and on removal of the applied force, the perimeter region exerts a restorative force to return to the rest configuration, such that the restorative force aids in retention of the wearable therapy apparatus in a desired position about the eye of the user.

Additionally or alternatively, the perimeter region may be flexible in at least one direction to allow a user to apply force and reduce the extent of the perimeter in the at least one direction to place the apparatus in the region of the eye of a user, further wherein the perimeter region is resilient to exert a force against the skin and/or bones surrounding the eye of the user, to mechanically hold the apparatus over the eye of the user without the use of an earpiece or strap.

Additionally or alternatively, the perimeter region may comprise a compression member that the user can compress for purposes of placing the therapy apparatus in the region of the eye of a user. Additionally or alternatively, the compression member may be a spring. Additionally or alternatively, the compression member may be a shape memory alloy member. Additionally or alternatively, the compression member may be a canister holding a fluid adapted to be compressed. Additionally or alternatively, the compression member may be a foam or sponge member.

Additionally or alternatively, the apparatus may further comprise an adhesive piece sized and shaped for placement over the perimeter region and configured to provide adhesion between the perimeter region and the skin of a user. Additionally or alternatively, the adhesive piece may be disposable. An illustrative kit may comprise the wearable therapy apparatus of the first illustrative and non-limiting example, and a sheet or roll having a plurality of adhesive pieces removeably disposed thereon, the adhesive pieces being double sided. Additionally or alternatively, the apparatus may be configured to be placed over only one eye of a user. Additionally or alternatively, the apparatus may comprising a multi-layer structure with a palpebral layer, an electronics layer, and an outer layer, the electronics layer comprising wire connections to couple the electrodes to the electronics module. Additionally or alternatively, the multi-layer structure may form or make up the field region and at least a portion of the perimeter region.

Additionally or alternatively, the perimeter region and field region may make up a first eyepiece having at least a first electrode, and the apparatus may further comprise a second eyepiece coupled to the first eyepiece by a nosepiece, the second eyepiece having at least a second electrode, wherein the electronics module is electrically coupled to each of the first and second electrodes. Additionally or alternatively, the electronics module may be located on a remote electrode that attaches to the body of a user distant from the eye, and is coupled by a wire to one of the nose piece or the first or second eyepieces. Additionally or alternatively, the electronics module may be carried on the nosepiece or on one of the eyepieces. Additionally or alternatively, the electronics module may be configured to be removed from the therapy apparatus. Additionally or alternatively, the nosepiece may carry one or more electrical connectors coupling the first eyepiece to the second eyepiece. Additionally or alternatively, each of the first and second eyepieces may comprise a separate electronics module, and the nosepiece provides a wire providing common ground reference to the electronics modules.

Additionally or alternatively, the apparatus may comprise a remote electrode coupled by a wire to the wearable therapy apparatus. Additionally or alternatively, the remote electrode may carry a battery, and the wire connects the battery to the electronics module to power the electronic module. Additionally or alternatively, the electronics module may be removeable. Additionally or alternatively, the electronics module may comprise a battery, and the battery is replaceable. Additionally or alternatively, the electronics module may comprise a rechargeable battery and a resonant element adapted to receive power via wireless transmission for recharging the battery.

Additionally or alternatively, the electronics module may comprise a rechargeable battery, further comprising external contacts adapted to receive power from a storage case having corresponding contacts for recharging purposes. A system example may comprise such a therapy apparatus and a storage case having the corresponding contacts. In the system example, the storage case may comprise a user interface for allowing a user to determine charge status the electronic module rechargeable battery. Additionally or alternatively, the storage case may comprise a user interface for allowing a user to set or modify stimulus settings of the electronics module.

Additionally or alternatively, the electronics module may comprise a rechargeable battery and a port adapted to receive a plug on the end of a charging cord, or on the end of a charging and reprogramming cord. Additionally or alternatively, the electronics module may comprise a battery circuit having one rechargeable battery cell or a plurality of rechargeable battery cells, either in one battery or in a battery stack, configured, at full charge, to provide about 10 to about 20 milliamp hours of current capacity at an output voltage of 6 volts or more, capable of providing at least two milliamps of constant current for a duration of at least 30 minutes.

Additionally or alternatively, the electronics module may lack any battery and comprises a resonant element adapted to receive power via wireless transmission for recharging the battery, a capacitor to receive power from the resonant element, and a switch configured to close when the capacitor holds enough energy for a stimulus output to be delivered.

Additionally or alternatively, the wearable therapy apparatus may have a mass of less than about 25 grams. Additionally or alternatively, the wearable therapy apparatus may have a mass of less than about 15 grams. Additionally or alternatively, the wearable therapy apparatus may have a mass of less than about 10 grams. Additionally or alternatively, the wearable therapy apparatus may have a mass of about 5 to about 25 grams. Additionally or alternatively, the wearable therapy apparatus may have a mass of about 5 to about 15 grams. Additionally or alternatively, the wearable therapy apparatus may have a mass of about 3 to about 10 grams.

Additionally or alternatively, the apparatus may comprise a temperature sensor configured to prevent activation of the electronics module when the wearable therapy apparatus is not on a user's body by sensing body temperature. Additionally or alternatively, the apparatus may comprise a temperature sensor configured to activate stimulus by the electronics module when the wearable therapy apparatus is on a user's head by sensing body temperature. Additionally or alternatively, the apparatus may comprise a motion sensor to sense user motion and determine whether stimulus delivered by the electronics module through the electrodes is causing muscle recruitment.

Additionally or alternatively, the electronics module may be configured to sense impedance between the electrodes. Additionally or alternatively, the electronics module may be configured to use sensed impedance to determine whether the wearable therapy apparatus is being worn by a user and, if so, to automatically deliver therapy. Additionally or alternatively, the electronics module may be configured to use sensed impedance to determine whether the wearable therapy apparatus is being worn by a user and, if not, to automatically disable therapy.

Additionally or alternatively, the electronics module may include a light indicator placed to indicate to a user whether the wearable therapy apparatus is delivering stimulus. Additionally or alternatively, the apparatus may be configured to deliver stimulus without the use of a remote return electrode. Additionally or alternatively, the apparatus may be configured to deliver stimulus with the use of a remote return electrode.

Additionally or alternatively, the stimulus output may be monopolar, bipolar, or other multipolar (such as tripolar), and the stimulus output may be monophasic, biphasic, or other multiphasic (such as triphasic). Additionally or alternatively, the stimulus output may comprise a first train of monophasic output pulses, and a second train of monophasic output pulses of polarity opposite the first train. Additionally or alternatively, the stimulus output may comprise a carrier signal modulated by an envelope, the carrier signal being operated at a first frequency and the envelope at a second frequency, wherein the second frequency is lower than the first frequency. Additionally or alternatively, the output stimulus may be voltage controlled, current controlled, or otherwise controlled for constant power. Additionally or alternatively, the electronics module may be configurable between a first configuration for current controlled output stimulus, and a second configuration for voltage controlled output stimulus.

A non-limiting first illustrative method example takes the form of a method of stimulating tissue to address a disease of the eye comprising placing a wearable therapy apparatus as in the first illustrative, non-limiting example and any of the variants thereof, about the eye of a user.

Additionally or alternatively to the first illustrative method, the perimeter region of the wearable therapy apparatus is flexible in at least one direction and has a rest configuration, such that a force applied to the perimeter region changes the shape of the perimeter region from the rest configuration, to facilitate placement about the eye of a user, and on removal of the applied force, the perimeter region exerts a restorative force to return to the rest configuration, such that the restorative force aids in retention of the wearable therapy apparatus in a desired position about the eye of the user, wherein the placing step comprises applying a compressive force to the perimeter region of the wearable therapy apparatus to change the shape of the perimeter region from the rest configuration, putting the wearable therapy apparatus at a desired position about the eye of a user, and releasing the compressive force and allowing the restorative force to aid in mechanical fixation of the wearable therapy apparatus in a target position about the eye of the user. Additionally or alternatively, the restorative force is exerted, at least in part, by a shape memory material that makes up a part of the wearable therapy apparatus. Additionally or alternatively, the restorative force is exerted, at least in part, by a sponge, a spring, or compressed air.

Additionally or alternatively to the first illustrative method, the perimeter region of the wearable therapy apparatus is flexible in at least one direction to allow a user to apply force and reduce the extent of the perimeter in the at least one direction in order to place the apparatus in the region of the eye of a user, further wherein the perimeter region is resilient to exert a force against the tissue surrounding the eye of the user, to mechanically hold the apparatus over the eye of the user without the use of an earpiece or strap, and the placing step is performed by applying a placement force to the wearable therapy apparatus to reduce the extent of the perimeter in the at least one direction and then releasing the placement force to allow the perimeter region to exert a staying force against the tissue surrounding the eye of the user. Additionally or alternatively, the staying force is exerted, at least in part, by a shape memory material that makes up a part of the wearable therapy apparatus. Additionally or alternatively, the staying force is exerted, at least in part, by a sponge, a spring, or compressed air. Additionally or alternatively to the first illustrative method, the placing step may be performed without the use of an earpiece or strap to hold the wearable therapy apparatus in position.

Additionally or alternatively to the first illustrative method, the method may comprise activating the wearable therapy apparatus to deliver the stimulus via one or more electrodes placed about the eye of the user. Additionally or alternatively, the wearable therapy apparatus comprises a temperature sensor and the activating step occurs automatically when the electronics module senses a temperature change by monitoring an output or characteristic of the temperature sensor. Additionally or alternatively, the wearable therapy apparatus comprises a button or touch surface adapted to sense touch, and the activating step occurs in response to the button being depressed or the touch surface sensing a touch. Additionally or alternatively, the electronics module comprises or is coupled to a communication circuitry for at least receiving an activation signal, and the activating step occurs when the electronics module recognizes the activation signal, further wherein the activation signal is issued by a smartphone, tablet, computer, or dedicated programming device.

Additionally or alternatively to the first illustrative method, the method may also comprise placing an adhesive piece on at least a portion of the tissue contacting surface of the wearable therapy device to provide fixation force to hold the wearable therapy device in a target position on the patient.

A non-limiting second illustrative method for treating a disease of the eye comprises administering a pharmaceutical or biological agent to the eye; and applying electrical stimulation to the eye using a wearable therapy apparatus as in the first illustrative and non-limiting example and/or any variant thereof.

A non-limiting third illustrative method for treating a disease of the eye comprises administering a pharmaceutical or biological agent to the eye; and applying electrical stimulation to the eye using a wearable therapy apparatus.

Additionally or alternatively to the non-limiting second or third illustrative methods, the pharmaceutical or biological agent may be a stem cell or plurality of stem cells. Additionally or alternatively to the non-limiting second or third illustrative methods, the pharmaceutical or biological agent may be a pharmaceutical agent. Additionally or alternatively to the non-limiting second or third illustrative methods, the electrical stimulation may be applied before the administering step is performed, such as anywhere from 0 to 96 hours. Additionally or alternatively to the non-limiting second or third illustrative methods, the electrical stimulation may be applied between 0 and 96 hours after the administering step is performed. Additionally or alternatively to the non-limiting second or third illustrative methods, the electrical stimulation may aid in addressing the disease of the eye when used in combination with the pharmaceutical or biological agent. Additionally or alternatively to the non-limiting second or third illustrative methods, the electrical stimulation may aid in absorption or effectiveness of the pharmaceutical or biological agent. Additionally or alternatively to the non-limiting second or third illustrative methods, the electrical stimulation may reduce a side effect of the pharmaceutical or biological agent. Additionally or alternatively to the non-limiting second or third illustrative methods, the pharmaceutical or biological agent is administered to the vitreous. Additionally or alternatively to the non-limiting second or third illustrative methods, the pharmaceutical or biological agent is administered to the retina.

A non-limiting container example takes the form of a container configured to receive a wearable therapy apparatus, the wearable therapy apparatus comprising one or more electrical contacts that are externally accessible, the container comprising a well having a shape that matches an outer perimeter shape of the wearable therapy apparatus, and one or more receiver contacts placed to electrically couple to the one or more externally accessible electrical contacts of the wearable therapy apparatus. Additionally or alternatively to the container example, the container may have an outer shell defining and interior and an exterior, the exterior comprising a user interface that is adapted to indicate charge and/or programming status of a wearable therapy apparatus contained therein. Additionally or alternatively to the container examples, the container may further comprise a power supply for providing power for recharging the wearable therapy apparatus, wherein the power supply is at least one of line powered, rechargeable battery, or primary cell battery.

Yet another illustrative and non-limiting example takes the form of a wearable therapy apparatus for placement about an eye of a user comprising a tissue contacting region sized and shaped for placement about the eye, the tissue contacting region comprising at least one electrode thereon for contacting the skin of a user, wherein the tissue contacting region is deformable to allow compression thereof prior to placement about the eye of a user, such that release of the compression provides a mechanical force to the tissue surrounding the user's eye aiding in fixation in a desired position.

Another illustrative and non-limiting method example takes the form of method of delivering energy to address a condition of the eye comprising placing a wearable therapy apparatus about the eye of a user, and activating the wearable therapy apparatus, wherein the wearable therapy apparatus comprises: a perimeter region including a tissue interface having at least one electrode, the perimeter region having a superior edge, and an inferior edge and at least one electrode, the perimeter region sized and shaped for placement about the eye of the user with the superior edge superior to the eye and the inferior edge inferior to the eye; a field region defined within the perimeter region; and an electronics module electrically coupled to the at least one electrode, the electronics module adapted to deliver electrical stimulus to the user through the at least one electrode, wherein the electronics module is carried on at least one of the perimeter region or the field region.

Additionally or alternatively the electronics module comprises a rechargeable or replaceable battery coupled to a pulse generator circuit adapted to generate output pulses, the pulse generator circuit having at least one output coupled to the at least one electrode, and a control circuit configured to determine timing pulse parameters for the output pulses of the pulse generator, wherein the activating step comprises: the control circuit issuing a test signal to determine tissue contact using the at least one electrode; and in response to confirming tissue contact with the at least one electrode, the control circuit controlling the pulse generator to issue output pulses as therapy.

Additionally or alternatively the perimeter region is flexible to allow compression thereof in a superior-inferior direction prior to placement about the eye of a user, such that release of the compression provides a mechanical force to the tissue surrounding the user's eye aiding in fixation in a desired position; and the method further comprises a user compressing the perimeter region, placing the wearable therapy device about the eye, and releasing the perimeter region such that the flexible perimeter region provides mechanical force to the tissue surrounding the users eye to hold the wearable therapy device in a desired position.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5 is an exploded view of an illustrative wearable therapy apparatus;

FIG. 6a is an elevation view of a palpebral surface of an illustrative wearable therapy apparatus, and FIG. 6b is an elevation view of an adhesive element for use with the apparatus of FIG. 6a;

FIG. 7a shows an illustrative system having a wearable therapy apparatus with a remote electrode and a case, and FIG. 7b shows an alternative structure to FIG. 7a;

FIGS. 8-10 show illustrative electrical architectures for wearable therapy apparatuses;

FIG. 11 shows a user with an illustrative wearable therapy apparatus;

FIG. 12 shows an illustrative wearable therapy apparatus and adhesive element;

FIGS. 13a-13c, 14a-14d, 15a-15c, 16a-16c, and 17 each show illustrative wearable therapy apparatuses.

DETAILED DESCRIPTION

Figure 1:
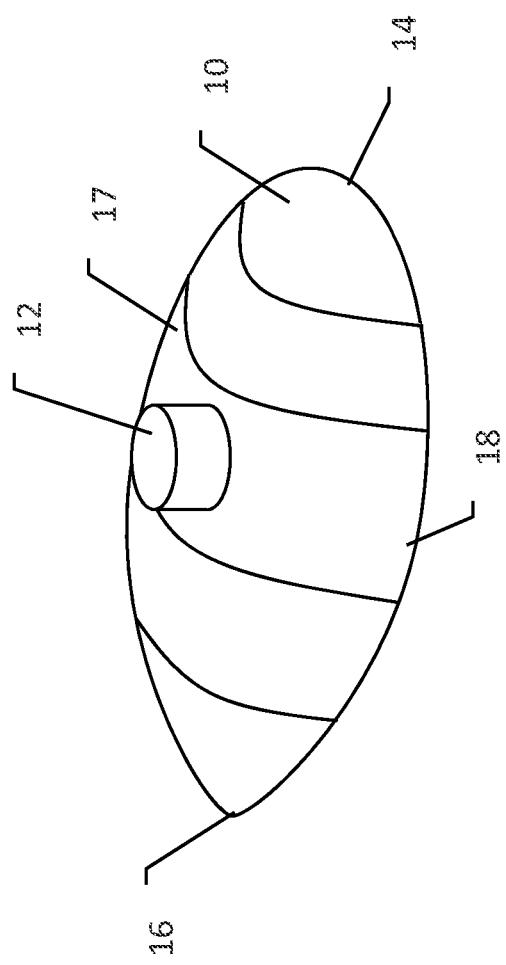
FIG. 1 shows an illustrative wearable therapy apparatus in a perspective view.

The present invention is generally directed to systems for delivering stimulus to the eye of a patient or user. Some patients may have a disease of the eye, such as one or more of the following: macular degeneration, inherited retinal disease, presbyopia, diabetic retinopathy, glaucoma, retinitis pigmentosa, Stargardt's, CMV-retinitis, Best's disease, macular dystrophy, optic neuritis, ischemic anterior optic neuritis, Usher's syndrome, Leber's congenital amaurosis, cone-rod dystrophy, cone dystrophy, choroideremia and gyrate atrophy, central retinal artery occlusion, central retinal vein occlusion, branch retinal artery occlusion, branch retinal vein occlusion, central serous chorioretinopathy, cystoid macular edema, ocular histoplasmosis, ocular toxoplasmosis, retinopathy of prematurity, amblyopia, strabismus, and nystagmus. Other patients may have different conditions that may be treatable by delivery of therapeutic energy to the eye and tissue near the eye. In addition or alternative to vision disorders, some illustrative conditions may include dry eye, headaches, migraine headaches, sleep disorders, fatigue, difficulty focusing or concentrating, problems with blinking, undesired movements (tics or twitching, for example). In some examples, a preventative therapy may be provided for persons who have not been diagnosed with a condition but who may be predisposed for such conditions, such as for patients with genetic markers, family history, or other medical conditions such as diabetes that increase the risk of vision disorders.

In some examples, new systems and methods for delivering electrical stimulus to a user may be used as a stand-alone therapy, or may be combined with other stimuli or therapy, such as light stimulus and/or cellular, biological, and/or pharmaceutical agents, for therapeutic or preventive reasons. Some examples are suitable for use in ocular modulation. As used herein, "ocular modulation" includes the application to the eye of an electrical signal, delivered non-invasively, or minimally-invasively, to achieve a therapeutic benefit. Therapeutic benefit may include, for example and without limitation, improving or altering blood flow, upregulating or downregulating synthesis, degradation, binding, release or activity of proteins, enzymes, DNA, RNA, polysaccharides or other endogenous physiological or pathological biomolecules; and/or upregulating, downregulating, activating, deactivating physiological or pathological biopathways, etc. Ocular modulation may be combined with the administration of pharmaceuticals, exogenously derived biomolecules, cell therapy, or photo-, electro- or magneto-reactive or active particles, such as nanoparticles, before, during or after an electrical signal is applied.

In some examples, the devices and systems disclosed herein are suited for use in conjunction with exogenous and/or endogenous stem cell transplantation therapies. For example, a method may comprise delivery of electrical stimulation before, during, or after stem cell transplantation to improve cell survival, repair and/or replacement. In illustrative examples, the use of methods and systems disclosed herein may enhance native cell survival, transplanted cell survival, transplanted cell integration, and functional synapse formation and/or axon regeneration. Non-limiting examples of endogenous stem cell types which may be suitable for transplantation in combination with systems or devices of the present invention include Müller cells, retinal pigment epithelial cells (RPE cells) and ciliary pigmented epithelial cells (CPE). Non-limiting examples of exogenous stem cells suitable for transplantation according to some embodiments of the invention include neural stem cells (NSCs), mesenchymal stem cells (MSCs) derived from bone marrow, adipose tissue or dental pulp and stem cells from the inner cell mass of the blastocyst and induced pluripotent stem cells (iPSCs). See, for example, "Using Electrical Stimulation to Enhance the Efficacy of Cell Transplantation Therapies for Neurodegenerative Retinal Diseases: Concepts, Challenges, and Future Perspectives", Abby Leigh Manthey, et al., Cell Transplantation, Vol. 26, pp. 949-965, 2017.

In some examples, a combination of methods or therapy systems of the invention with biological or pharmaceutical agents may provide improved efficacy or reduced side effects associated with such biological or pharmaceutical agents when administered alone. Pharmaceutical agents currently used to reduce the growth of new blood vessels in wet AMD include anti-angiogenics such Bevacizumab (Avastin®), Ranibizumab (Lucentis®) and Aflibercept (Eylea®), etc. While the benefit of these agents for mitigating symptoms associated with wet AMD are well-known, these agents also may have side effects including increased eye pressure, inflammation of the eye and others. A benefit of systems disclosed herein includes modulation of cytokines and other endogenous inflammatory factors involved in the inflammation process. In some embodiments it is foreseen that administration of anti-angiogenic agents listed above or other pharmaceuticals in combination with electrical therapy applied simultaneously with, before (e.g. 1, 2, 12, 24, 36, 48 and/or 96 hours before), or after (e.g. 1, 2, 12, 24, 36, 48 and/or 96 hours after), injection of such anti-angiogenics, at stimulation parameters used herein, may beneficially improve the efficacy and/or reduce the likelihood of side effects associated with administration of such agents.

Several different modes of energy delivery can be used including mechanical delivery (such as sonic energy, including for example, ultrasound), light-based delivery (such as by the delivery of collimated or non-collimated light of selected wavelengths, for example using a laser, a light emitting diode, etc.), electrical delivery (such as by the delivery of an electrical signal), and/or magnetic delivery (such as by generating a magnetic field or fields). In some examples, one mode of therapy delivery is used, while the same or a different mode is used to monitor therapy delivery. One component of several examples is the use of configurations that are adapted to provide enhanced tissue contact, enhanced therapy delivery, targeted therapy locations, improved user comfort and/or to compliance, and/or reduced likelihood of tissue injury or irritation.

Various features for delivering therapy may be understood by review of, for example and without intending limitation, U.S. Pat. No. 7,251,528 to Harold, U.S. patent application Ser. No. 16/589,383, titled SYSTEM AND METHODS FOR CONTROLLED ELECTRICAL MODULATION FOR VISION THERAPY, and Ser. No. 16/697,689, titled HEAD WORN APPARATUSES FOR VISION THERAPY, the disclosures of which are incorporated herein by reference as showing waveforms, structures, apparatuses and systems for delivery of ocular modulation.

Figure 2:
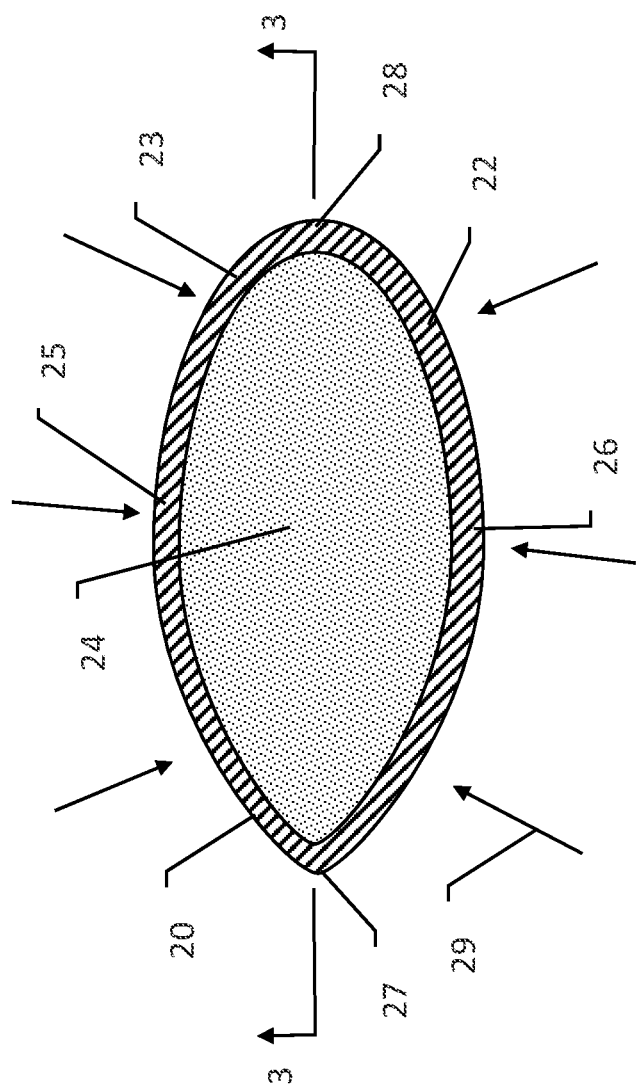
FIG. 2 is an elevation view of a palpebral surface of an illustrative wearable therapy apparatus.
Figure 3:
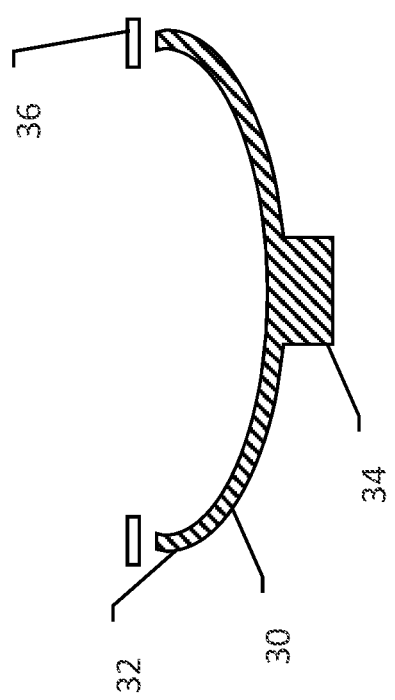
FIG. 3 is a section view of the wearable therapy apparatus of FIG. 2.

FIGS. 1-3 show an eyepiece 10, 20, 30 that can be used to deliver electrical stimulation, such as ocular modulation, to a user. FIG. 1 shows the outer side of the eyepiece 10, which includes a protrusion 12 more or less in the middle thereof, an outer edge 14 and an inner edge 16. In this example, the eyepiece 10 is shown as being somewhat asymmetrical to conform to the shape of the eye of a user. The overall shape may be modified or personalized as desired. For example, the eyepiece may come in a variety of shapes and sizes, or may be custom made for a given user by, for example, creating a custom mold or by the use of a combination of imaging and rapid prototype or three dimensional printing. The protrusion 12 is optional but may be used in several examples as a central position to house electronics of the device, as well as to allow a user to readily place or remove the product from the eye by grasping the protrusion 12.

The inner edge 16 may be for placement adjacent the nose and may be referred to as a nasal edge, while the outer edge 14 may be placed closer to the temple and may be referred to as a temporal edge. The eyepiece 10 includes a superior edge 17 and an inferior edge 18. In some examples, the eyepiece 10 is generally flexible or elastomeric and can be deformed in order to facilitate placement over the eye. For example, an elastomeric or flexible structure may be compressed manually, placed over the eye, and released. As the structure recovers from compression it may come to rest and mechanically fix itself against the bony and/or muscular tissues around the eye. In other examples, a reusable or replaceable adhesive may be used to hold the eyepiece over the eye of a user by placing such on one or more surfaces of the outer, inner, superior and/or inferior edges 14, 16, 17, 18. In still other examples, both adhesive and mechanical retention may be used.

FIG. 2 shows the back or palpebral surface (the surface adjacent to the eyelid) of an eyepiece 20 generally similar to that of FIG. 1. The eyepiece 20 includes a perimeter region 22 and a field region 24 spaced away from the eye to reduce contact with the eye, eyelids, and/or eyelashes. The perimeter region 22 includes a superior edge 25, inferior edge 26, nasal edge 27 and temporal edge 28. The perimeter region 22 may contact the eyelids or tissue surrounding the eyelids, such as the upper cheek. Electrical therapy may be delivered via the perimeter region 22, while other therapy that can be delivered without contacting the skin, such as light therapy or magnetic field therapy, may be generated in the perimeter region 22 and/or in the field region 24.

In another example, rather than a field region that is separated from the eyelids, a greater portion of the palpebral surface may contact the eyelids, facilitating electrical therapy delivered therethrough. For example, current may be directed to the eyeball directly beneath the eyelid, rather than using electrical (or other) therapy directed from the perimeter region 22. For such an example, there may be one or more slits or perforations in the field region to allow the eyelashes to pass through, avoiding the possibility of the eyelashes interfering with tissue/electrode contact.

Returning to the illustrative example in FIG. 2, the field region 24 may be opaque or clear, or may be photochromic or electrochromic, as desired. For example, the eyepiece may be electrochromic to be generally transparent when therapy is not being delivered, and a magnetic or electrical field can be generated during therapy delivery to render the field region 24 opaque or semiopaque. Some examples may omit the field region 24, such that only a perimeter region 22 is provided.

The perimeter region 22 may include a contact surface 23 designed to be comfortable and non-irritating to the user's skin. For example a contact surface 23 may be include a soft foam or gel interface, such as having a gel encapsulated in a thin film such as a polyurethane film, holding a polyurethane gel. In other examples a soft foam, preferably non-latex, is used for tissue contact. In some examples, the eyepiece 20 may include different regions of different resiliency, strength and/or softness, such as by having a central region that is more structural and holds a desired shape, while the portions closer to the perimeter region that contacts the skin are softer to limit or prevent skin irritation and enhance comfort. The perimeter region 22, as further shown below, may include one or more electrodes thereon to deliver electrical therapy to the user in the form of optical modulation or microcurrent therapy to address vision related disorders.

In an example, the eyepiece 20 perimeter region 22 may be configured to flex more in a superior-inferior direction, i.e., edges 25/26 can be moved closer to one another, than in a nasal-temporal direction. That is, the user may be able to squeeze the device more in one direction than the other, for placement in a desired position about the eye of a user. In another example, the field region, or a portion thereof, may also be flexible, with the field region being easier to flex in the superior-inferior direction than it is in the nasal-temporal direction. In another example, the perimeter region 22 may vary in flexibility or softness in a circumferential manner such as by having the nasal edge 27 formed of a first material with one or more other edges 25, 26, and 28 formed of a different material having different properties (such as softness, resiliency, elasticity), for example.

Arrows 26 in FIG. 2 indicate that a user wishing to place the device 20 may simply squeeze the outer edges of the device inward, and then insert the apparatus within or around the eye socket. When the edges are released, the outer edges will press against one or more of bones forming the eye socket (such as the frontal, zygomatic, or maxillary bones) to hold the apparatus in position. Use of a mechanical approach to securing the eyepiece 20 in place in the eye socket is illustrative; some examples may use an adhesive rather than a mechanical approach. In some examples, both adhesive and mechanical securing may be used. In an example, a mechanical force may generally hold the eyepiece in place, while the adhesive force is used to aid in keeping electrodes of the product in electrical contact with the skin of the user, either as dry electrodes or through a gel or other intervening substance (other than air).

In some examples, the perimeter region may comprise a spring-loaded frame allowing for compression to place the device 20 by compressing one or more of the superior edge 25, inferior edge 26, nasal edge 27, or temporal edge 28, or elsewhere, to contract the device against a spring load for placement. (See FIG. 17, below). In still another example, a spring loaded mechanism(s) may be actuated by a handle portion that extends away from the device 20, allowing the user to pinch the handle and thereby compress the perimeter against spring forces for placement.

In a further example, the aim may be to achieve an airtight seal against the skin around the eye, such as used with goggles for swimming. Thus, air pressure can be used instead of, or in addition to, mechanical and/or adhesive fixation. For example, suction may be applied once the eyepiece is in a desired position to hold the eyepiece in place.

Figure 18:
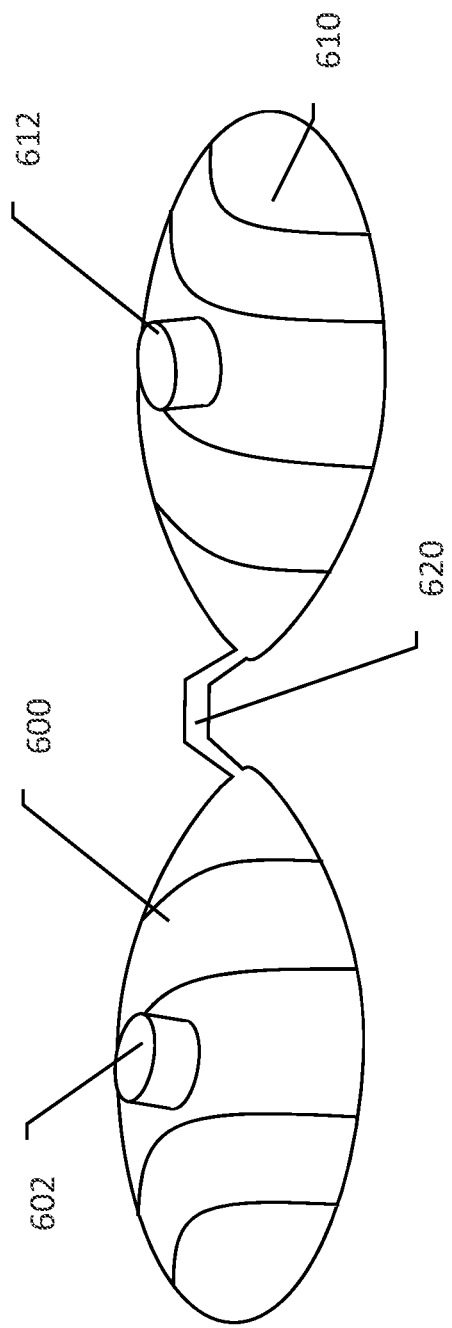
FIGS. 18-19 show illustrative systems having a nosepiece coupling together two illustrative wearable therapy apparatuses for placement about the eye.
Figure 19:
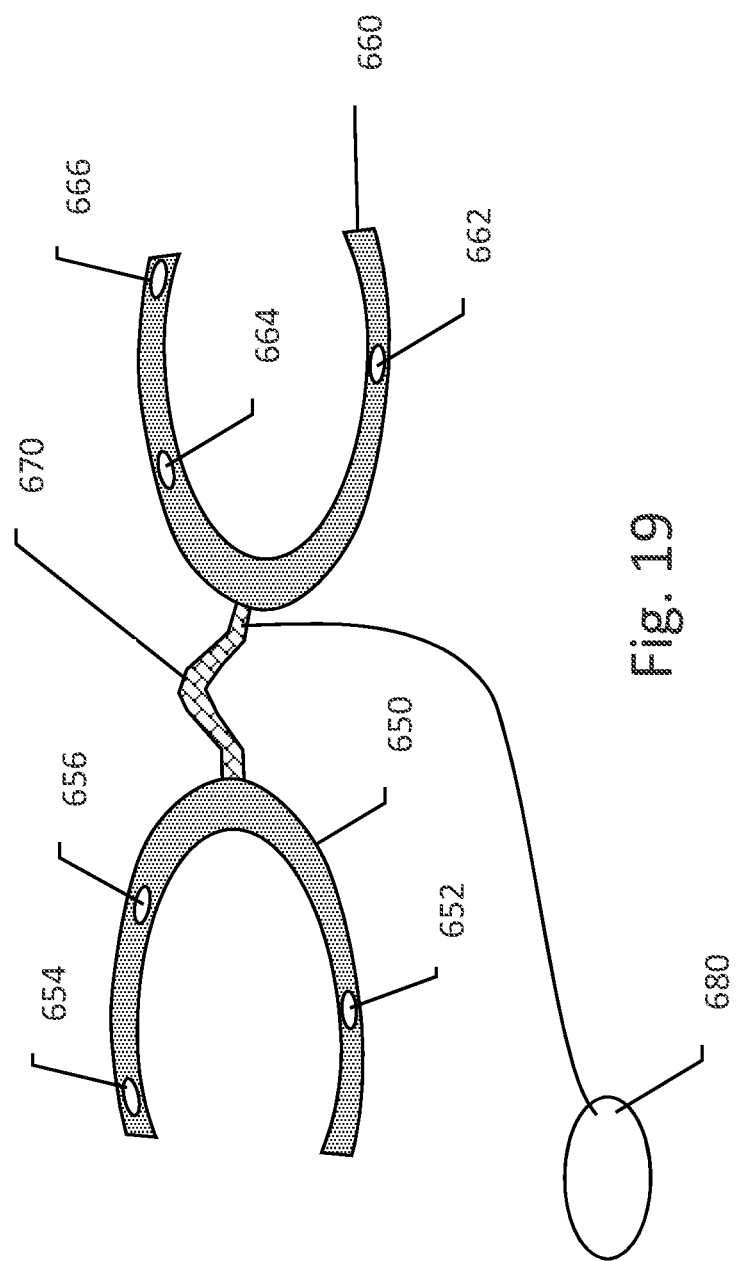

Some illustrative examples comprise any of the device designs shown herein, without the need for an earpiece or strap that facilitates retention around the eye by mounting to or around the ears and/or by wrapping the entire way around the head to hold the eyepiece or goggles in place. In other examples, one or both of a strap or earpiece may be used, as desired. A nosepiece to aid in retention, support or stability, or simply to link together two eyepieces mechanically and/or electrically, may be included if desired, though several examples do not use a nosepiece. A nosepiece may be used with a single eyepiece, if desired, or may couple two eyepieces together as shown in FIGS. 18-19.

A section view of a device similar that of FIG. 2 along line 3-3 is shown in FIG. 3. This illustrative eyepiece 30 has a perimeter region 32 which, as noted above, may comprise a relatively soft material such as a foam or a gel, and also includes the protrusion 34. As shown below in FIG. 5, the protrusion may be hollow if desired to house electronics therein. In some examples, the protrusion 34 may be useful to provide the user an easy place to grab the eyepiece for removal from the eye or for removal from packaging. The protrusion may include a port to receive a plug from a charging station to allow recharging of a power supply. In another example, rather than a port, a receiver for wireless charging may be provided, such as an inductive coil or an antenna.

As noted above, and shown in FIG. 3, a reusable or replaceable adhesive piece 36 may be included. For example, the adhesive piece 36 may be a double sided medical grade tape, for example, adapted to stick both to the skin of a user and to the perimeter region 32 of eyepiece 30. In some examples, the adhesive piece 36 is provided in packs of oval or almost circular pieces, or other shape, designed to match the eyepiece 30. In other examples the adhesive piece 36 may be omitted. In another example, permanent or replaceable thin film membrane(s) that carry a dry electrode may be included.

Figure 4:
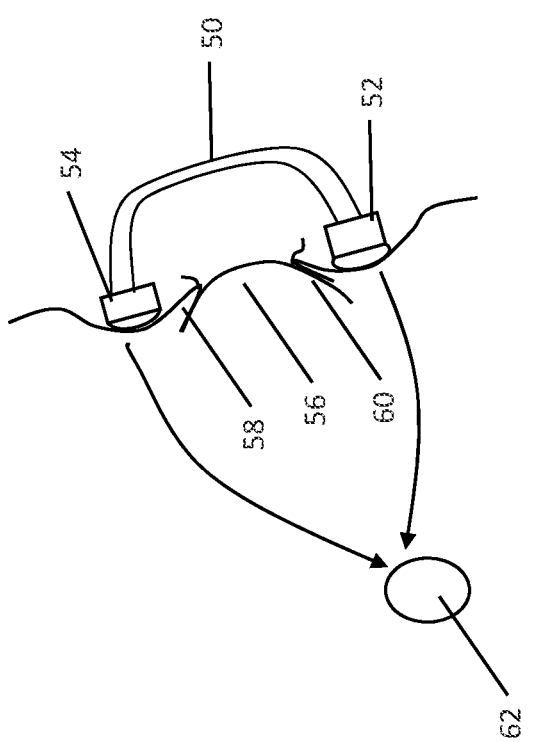
FIG. 4 is a side view of an illustrative wearable therapy apparatus on a user's eyelid.

FIG. 4 shows another example of an eyepiece, as placed over a user's eye and viewed in side section. Here, the eyepiece 50 has an inferior portion 52 shaped to contact the lower eyelid 60, and a superior portion 54 shaped to contact the upper eyelid 58. The inferior and superior portions 52, 54 may provide mechanical fixation by pressing against the bony ridges of the eye socket, such as by pressing against one or more of the frontal, zygomatic, or maxillary bones that surround the eye. The eye 56 can be opened or closed with the eyepiece 50 in position.

Structurally, the example shown in FIG. 4 suggests an eyepiece with a relatively flattened field region. If desired, the eyepiece may comprise an outer portion that serves as a holder for a central lens, wherein the central lens may be a vision-correcting lens. For example, if the user ordinarily wears corrective lenses (contact lenses or glasses for example), the eyepiece 50 may include a corrective lens. The corrective lens may be a built in or integral piece, may be formed along with the rest of the eyepiece such as by molding or three-dimensional printing, or may be a separate element that the eyepiece can receive. In this way, the eyepiece 50 may allow ambulation by the user during therapy, or may allow the user to watch television, read a book, or perform other tasks during therapy. In other examples, the field region may be more rounded and/or hemispherical.

As shown in FIG. 4, there may be target tissue region 62, such as the optic nerve or macula, or any other target desired, to which current and/or electrical field is to be directed. The target may be at a different position than that shown.

In some examples, a bipolar electrode approach is taken, without the use of a remote return electrode. For example, an electrode in the inferior region 52 may serve as anode, while an electrode in superior region 54 may serve as cathode, for therapy delivery (or the usage may be reversed). In other examples, a monopolar therapy can be delivered, using one or more electrodes on one or more of the inferior and/or superior regions 52, 54 as anode or cathode, and a remote electrode elsewhere on the user, such as on the head, the neck, the shoulder, torso or a limb. For example, a return electrode may be on the user's arm, hand, shoulder, chest, neck, mouth, ear, or temple of the user. A biphasic therapy may be delivered, allowing for charge balancing of the output and making use of each electrode as both anode and cathode during therapy delivery. In still further examples, both biphasic and monophasic therapy are delivered, for example, in a patterned therapy using each type of therapy delivery in alternating or cyclic fashion. In an example, monophasic therapy may be provided for a fixed period of time, with subsequent phase reversal and further delivery for another fixed period of time, avoiding over-polarization, which could lead to, for example, muscle recruitment or may encourage corrosion or other damage to the electrode-tissue interface. Phase reversal may in some examples enhance therapy efficacy.

In an example, a plurality of electrodes are disposed on one or the other, or both, of the inferior and superior regions 52, 54, such as shown below in FIGS. 6a-6b. For example, there may be electrodes I1 and I2 on the inferior region 52, and electrodes S1 and S2 on the superior region 54. Assuming no other electrodes, and using "off" to indicate that an electrode is in a high impedance state and not connected to a voltage or current source, some illustrative combinations include:

| Combination | I1 | I2 | S1 | S2 |
|---|---|---|---|---|
| A | Anode | Off | Off | Cathode |
| B | Off | Anode | Off | Cathode |
| C | Anode | Anode | Off | Cathode |
| D | Anode | Off | Cathode | Off |
| E | Off | Anode | Cathode | Off |
| F | Anode | Anode | Cathode | Off |
| G | Anode | Off | Cathode | Cathode |
| H | Off | Anode | Cathode | Cathode |
| I | Anode | Anode | Cathode | Cathode |

Additional combinations may be defined by reversing polarity for each of the labeled combinations, and, in addition, there may be combinations where a superior electrode is opposed to another superior electrode, with or without an inferior electrode receiving or delivering current/voltage, or, alternatively, where an inferior electrode is opposed to another inferior electrodes, with or without a superior electrode receiving or delivering current/voltage. In some examples, an "anode" output indicates a voltage (or current) applied relative to reference, wherein the cathode is at the reference voltage; in other examples, the cathode may be at a voltage (or current) opposite that being applied by the anode. In examples where both anode and cathode are at non-reference voltages (or are actively current sources and sinks), one or more "off" electrodes may be coupled to reference rather than a high impedance state. An alternating or cyclic pattern may include any sequence of two or more such combinations.

Waveshape may vary. If desired, sinusoidal, triangular, ramped (up or down), exponential (up or down), or square waves may be delivered in any of current, voltage, or power controlled outputs. For example, a current controlled output may provide a square wave of constant current for its duration. In another example, a voltage controlled output may take the form of an exponentially decaying output. Other combinations and shapes may be used if desired. In some examples, an output circuitry of the electronics module may be configurable between a first configuration that delivers current controlled outputs and a second configuration that delivers voltage controlled outputs. For example, a first feedback loop may be provided that monitors voltage across the output electrodes (for voltage control), while a second feedback loop monitors voltage across a resistor (for current control) that is in series with the output electrodes, and the controlling circuitry such as a microprocessor, ASIC, or state machine, can be programmed to select one or the other of the feedback loops to use.

In some examples, the output waveform may comprise a modulated carrier wave, such as a modulated 1 Hz to 1 MHz output, shaped as a square wave; higher or lower frequencies may be used. In an example, a carrier wave takes the form of a square wave with a frequency of 1 kHz to 40 kHz and 50% duty cycle, modulated by an envelope signal of a lower frequency as discussed in U.S. Pat. No. 7,251,528, the disclosure of which is incorporated herein by reference. The duty cycle may be anywhere from 1% to 100%, if desired. The envelope may be a square wave in the range of about 1 to about 100 kHz, more preferably about 1 to about 1000 Hz, or about 1 to 400 Hz. In another example, the envelope may be at a selected one of 10, 20, 30, 40, 50, 100, 200, 300, 500 or 1000 Hz; other envelope frequencies may be used. In still another example, the user may receive a series of different frequency outputs, by varying the envelope frequency and/or varying the carrier frequency. The carrier wave or the envelope may be sinusoidal instead, if desired, or may have a different shape such as triangular, ramped, etc. In some examples, additional factors may be programmable parameters, such as duty cycle, pulse width of the carrier signal or envelope signal. In an example, a monopolar output is provided, with periodic changing of the polarity to maintain charge balance at the tissue interface. For example, some embodiments of a wearable therapy apparatus provide a stimulus output as a first train of monophasic output pulses of a first polarity, and a second train of monophasic output pulses of polarity opposite the first train. In other examples, therapy output may be allowed to leave a residual charge imbalance.

In another example, a therapy signal is provided with a frequency of about 1 Hz to about 1 MHz, and the combination of carrier and envelope is omitted. For example an output may be provided as a biphasic square wave with a frequency in the range of 10 Hz to 20 kHz, or about 100 Hz to about 15 kHz, with the output delivered for a fixed period of time such as 1 millisecond to about 1 hour, or about 100 milliseconds to about 30 minutes. The waveform may be delivered repeatedly, at fixed or random intervals, and may take other shapes including triangular, sinusoid, etc. Therapy signals may be delivered with a soft turn-on or ramp, in which the therapy output signal is ramped up from a starting level (such as 0 volts or 0 amps) up to the desired therapy level over the course of a few milliseconds to a few seconds, or longer. Other parameters including pulse width, off time, polarity switching frequency (if used), etc. may vary as well.

A programmable amplitude may be set as well using, for example, power, current or voltage as the controlled variable. In some examples, current may be delivered in the range of about 0.1 to 100 milliamperes, or in the range of about 1 to about 1000 microamperes, or in the range of about 300 to 500 microamperes, using any of the above noted parameters for waveshape, frequency, duty cycle, etc. Voltages may be in the range of, for example and without limitation, 1 millivolt to 50 volts, or more or less, and power may be in a range of up to about 1 watt.

The user may be allowed to freely modify parameters, or access may be restricted to a clinician user, or it may be that the user can modify parameters within a narrower range controlled by a clinician. For example, a clinician may be enabled to set current in a range of 1 to about 10,000 microamperes, while the user can only modify the current, once set by the clinician, within a range of plus/minus 300 microamperes, or more or less. Other specific settings may be used. In some examples, the user may not be allowed to change parameters.

In some examples, a closed loop approach may be taken wherein sensing circuitry in the apparatus is configured to sense select parameters of therapy delivery or sense other parameters, such a biological events. For example, it has been shown that users may experience flashes of light, known as phosphenes, during therapy. To allow a user to perform ambulatory or other activities, phosphenes may be avoided by having the device sense for phosphenes (a capability that has also been demonstrated in animal models) and reduce power output when phosphenes are sensed to limit the impact to a user's visual experience. Another approach may be to occasionally or periodically test a user's phosphene threshold, such as at the start of a therapy session, and then set therapy parameters to use duty cycle, amplitude, current density, or other factor so therapy stimuli is delivered at a level that is below the phosphene threshold. Such testing may further include having a user move his or her eye to different positions during threshold testing (i.e., looking up, down, left or right) by issuing one or more commands to the user to modify eye position during phosphene threshold testing.

The ability to select from various pairing of electrodes may be useful to provide therapy targeting separate conditions by selective use of the electrodes. For example, glaucoma is typically associated with fluid transport structures in the eye that are more superficial, anatomically, than structures associated with a condition such as macular degeneration. Therefore, in an example, relatively more closely spaced electrodes, or bipolar therapy regimens, may be used to treat glaucoma, while more greatly spaced electrodes, and/or monopolar therapy regimens may be used to treat macular degeneration, for a user having or at risk for both conditions.

In a still further example, a current flowing between two electrodes on one eyepiece may be useful in glaucoma patients to cause contraction or expansion of the ciliary muscle regions, opening the iris root and facilitating drainage through the trabecular meshwork. In some examples, a current applied by an eyepiece may energize a stent placed in the trabecular meshwork to aid fluid flow, or to energize a device placed elsewhere in the eye to cause other beneficial therapeutic effects such as heating, light or electrical stimulus affecting neural structures in the eye. In examples it is envisioned the bipolar electrode positioning around an eyepiece can provide selected stimulation to rehabilitate an atrophied ciliary muscle before or after implantation of an artificial intraocular lens. In still other examples, other structures in the head may be targeted, such as the optic nerve and/or targets in or around the brain, the sinuses, or the eye.

Multiple therapy patterns or programs may be set for a single device. For example, the electrical components may comprise a state machine or microprocessor architecture with stored states or stored instructions, respectively, to deliver pre-selected therapy patterns or types. Therapy patterns may be defined according to which electrodes are selected for use (and in which role—ground, anode, cathode, etc.), as well as waveform characteristics for each output channel (pulse width, frequency, amplitude, relative amplitude, pulse shape, duty cycle, inter-pulse intervals, burst patterns, etc.). Such patterns or programs may be set by a physician during a programming session using, for example, a clinician device such as a mobile phone, tablet or computer, or a dedicated programmer device, as desired.

U.S. Pat. No. 7,251,528 to Harold, U.S. patent application Ser. No. 16/589,383, titled SYSTEM AND METHODS FOR CONTROLLED ELECTRICAL MODULATION FOR VISION THERAPY, and Ser. No. 16/697,689, titled HEAD WORN APPARATUSES FOR VISION THERAPY are each incorporated herein by reference as showing various features electrical therapy (and other modes of energy delivery) directed to the eye. The designs and features discussed herein may be implemented in combination with the features of either the issued U.S. Pat. No. 7,521,528 patent or the Ser. No. 16/697,689 and Ser. No. 16/589,383 patent applications.

FIG. 5 shows an illustrative construction using a multilayer layer approach. The example shown has three layers, though any suitable number of layers may be included in other embodiments. An inner piece 70, which may form the palpebral surface, is provided along with an outer piece 90, which may form the external surface of the device. The inner and outer pieces 70, 90 can be secured together by known methods including, for example, snap fit, adhesive, or in some examples, simply mate together to mechanically secure to one another. The inner and outer pieces 70, 90 may be foam, polymer, other plastic, or any other suitable material. The inner and outer pieces 70, 90 sandwich electronics 80 therebetween. The outer piece 90 may include a void or receptacle 92 for receiving additional electrical components 82 of the eyepiece.

Electronics 80 may comprise connecting wires 84 and the tissue contacting electrodes 86. Sensing elements and/or transducers for outputting therapy (sonic, optical, magnetic) may be included in place of or along with electrodes 86. The electrical components 82 may, in an example, include a non-rechargeable battery that is replaceable through the open side of receptacle 92. In another example, the operational circuitry may include a rechargeable battery that can be recharged by plugging in a charging plug, which may be a standard plug such as mini-USB, or other standard design, type, or size, or may be custom plug. In another example, a storage case (FIG. 7, below) may comprise one or more contacts that couple with the receptacle 92, which may include contacts for recharging. In still another example, the operational circuitry may include a rechargeable battery that can be recharged wirelessly using magnetic/inductive charging, RF charging, or other charging medium/modality.

Any suitable chemistry or structure may be used for the batteries. For example, batteries similar to those used for hearing aid devices may be used, in either rechargeable or non-rechargeable forms. Chemistries such as Zinc-air, Nickel metal hydride (NiMH), Lithium-ion (Li-ion), and Silver-zinc (AgZn), may all be suitable in various embodiments. Additional lithium based technologies may be used, such as LiMNO2, Lithium cells may provide higher output voltages on a per cell basis, which may be useful for a microcurrent therapy apparatus that will likely encounter higher impedances (in the kilohms, for example). However, other factors such as cost and ease of disposal may also come into play when selecting a particular battery type and size. Total capacity, volume/footprint requirements, discharge curve characteristics and other factors may be considered as well. Multiple cells may be used in series and/or parallel to provide adequate voltage and current capacities for therapy purposes. Recharge of batteries may be performed by direct, wired connection or by wireless coupling of an inductive element or antenna, or any other suitable method.

In some examples, a battery may be omitted and a capacitor or supercapacitor used instead, allowing charging and discharging over time. For example, a receiving antenna or inductive coil may receive energy output by a remote device and the received power can be used to charge a capacitor. Once the capacitor is charged to a desired level, the capacitor can be discharged to deliver therapy to the user. A determination that the capacitor is at the desired level may be made by, for example, having a comparator in the system to compare to a reference voltage, or by having a silicon-controlled rectifier that, once the desired voltage level is reached, will close a switch allowing discharge of the capacitor and open again once the capacitor is discharged to at least a threshold amount.

In still other examples, therapy output may be generated by a separate power source with transmits power wirelessly, such as by RF or inductive power transfer, to power and trigger therapy outputs by the device. Here, the receiving element in the device may be more or less directly coupled to the output electronics and electrode(s). Each of these different electrical topologies are available in different examples, as illustrated below in FIGS. 9-11.

In the example of FIG. 5, the electronics 80 may be a modular unit which can be coupled to one or more user-specific pieces. For example, the inner and outer pieces 70 and 90 may be particularly sized or shaped for a given individual. In another example, the electrical components 82 may be detachable from the connecting wire 84 and electrodes 86, so that the entire apparatus other than the electrical components 82 may be discarded from time to time, for example, as adhesive or flex properties inner and outer pieces 70, 90, and/or at the tissue interface, degrade or reach end of useful life. Alternatively, the electrical components 82 may be discarded if, for example, a primary cell or non-rechargeable battery is used and becomes spent. In still another example, the entire assembly may be intended for extended or limited use, as, for example, if the electrical components 82 are designed to be used by the recipient for a week, a month, or several months, or other predetermined period of time. In yet another example, only a portion of the electrical components, such as the battery, may be removable, to allow discarding the battery once spent without discarding the rest of the apparatus.

Total mass of the eyepiece may be kept relatively small, such as in the range of less than about 50 grams, or less than about 25 grams, or less than about 15 grams, or less than about 10 grams, in order to make it easier for a mechanical and/or adhesive approach to securing the eyepiece in place readily achieved. In one example, the total mass of the eyepiece is in the range of about 5 to about 15 grams. In another example the total mass is about 5 to about 25 grams. Such masses may exclude the mass associated with gel-based contact enhancements. Some eyepieces that exclude a field portion (as in FIGS. 14d, 15c and 16c) may be somewhat lighter, in the range of about 3 to about 10 grams, though greater or lesser mass may be used if desired in these and other examples.

As a numerical and non-limiting example, the typical output for the system may be designed for a range of less than about two milliamps, delivered over the course of a 20 to 30 minute treatment session, into a load of 3000 ohms or less. The duty cycle may be in the range of 50% or less, even down to less than 10%, if desired. For example and without limiting the invention to these quantities/numbers, a 30 minute session at 2 milliamps average battery current would deliver current at a peak output amplitude of 6 volts. Zinc-related battery chemistries (zinc-air, or zinc-silver) are known and commercially available for hearing aids with output voltages in the range of 1.7-1.8 volts, while Lithium chemistries are typically closer to 3 volts. Commercially available hearing aid batteries, in rechargeable and/or non-rechargeable form can weigh less than one gram, some close to 0.5 grams, having a stored current capacity of ten or more milliamp hours. Thus, two such Lithium based cells, or four zinc based cells, could be used in series to provide the output desired (6+ volts and 1+ milliamp-hours) with a mass of just a few grams and a size of about 3 mm thickness and 7 mm circumference.

In some examples, a battery circuit comprises a plurality of rechargeable battery cells, either in one battery or in a battery stack, configured, at full charge, to provide about 10 to about 20 milliamp hours of current capacity at an output voltage of 6 volts or more, capable of providing at least two milliamps of constant current for a duration of at least 30 minutes, which would, in this non-limiting example, provide a system able to deliver therapy for a full week on one charge. Other examples may use different capacities and metrics, as well as different battery types, or no battery at all. Fabrication of a special purpose battery, for example having a plurality of battery cells within a single housing, may reduce mass relative to the use of off-the-shelf batteries, as well as providing a desired shape/footprint, if desired. As noted, the chemistries and numerical examples discussed are for purposes of illustration and are not limiting of the invention, unless specifically recited in the appended claims.

In an example, a progressive therapy regimen may be used for a user in which a series of eyepieces, each with a different set of pre-selected, fixed therapy parameters, are used over the course of time. For example, a first eyepiece in a set may use a first set of therapy parameters, and a second eyepiece in the set may use a second, different set of therapy parameters, wherein the user is instructed to use the first eyepiece for a first period of time (such as a week or a month), and then to switch to the second eyepiece. This may be useful to provide therapy with titration from lower intensity to higher intensity, or from higher intensity to lower intensity, over the course of weeks or months. In another example, therapy parameters may simply change, rather than increasing or decreasing in intensity, such as by modifying other features (pulse shape, pulse width, frequency, frequency combination, etc.). Rather than visiting a clinic to modify stored parameters in a long-term device, the user may instead receive a set of eyepieces or a new eyepiece from time to time. Such an approach may be similar to that used in orthodontics in which wearable braces are provided as a series of mouth pieces that the user is to wear for a limited period of time and then replace with a next piece in the series. For such a regimen, the actual eyepiece may be non-reprogrammable; basically having only an on/off functionality, if desired, though fuller programmability remains an option in other examples.

In another example, parameters such as stimulus frequency, pulsewidth, amplitude, electrode selection, and combinations thereof may be reprogrammable. In some examples, wireless reprogramming may be used, such as via any suitable wireless protocol and frequency (Medradio, Bluetooth, Bluetooth Low Energy, WiFi, cellular, inductive telemetry, IEEE 802 protocols, etc.), or by using, for example, optical (such as infrared communication) or magnetic coupling, or mechanical coupling (ultrasound, for example). Wired reprogramming may be used, for example, if the device comprises a port for plugging in a USB or micro-USB plug, or any other suitable coupling including both electrical and optical cables. Reprogramming may include selecting, or changing therapy parameters such as amplitude, pulsewidth, frequency, duty cycle, shape, ramping, electrode selection, pulse shape, pulse type (current controlled or voltage controlled, for example), and any other suitable characteristic.

A communication session may include retrieval of diagnostic information as well, such as electrical signal feedback, motion, impedance sensed at the electrodes, optical interrogation results, etc. For example, electrical signal feedback may be used to detect the occurrence of phosphenes, which may be useful to determine if intensity, amplitude, or frequency of stimulation, for example, are in a desired range. Some examples may use the occurrence of phosphenes as an indication that therapy is effectively stimulating target tissue or connected to the eye; other examples may seek to deliver therapy at an intensity, amplitude, and/or frequency that is below a threshold at which phosphenes occur. Phosphenes may also be reported by a user such as by having the user tap the eyepiece when a phosphene is observed, or by making an entry or otherwise actuating an external device adapted for wireless coupling to the eyepiece. Motion, sensed for example using a micro-size accelerometer, can be used to sense such tapping by the user/patient. Motion may also be used to determine whether and/or how, for example, the user's eye is moving during therapy, or during a diagnostic test (such as having the user track a moving object or image), or may be used to determine whether the user is experiencing any side effect, such as muscle recruitment, during therapy. For example, if the user receives therapy above a muscle recruitment threshold, the user may experience twitching in the area of the eye, which may be uncomfortable and would be sensed with a motion sensor. In response to sensed motion, therapy may be modulated to a lesser or different amplitude, intensity, frequency, pulse width, etc. In another example, an optical interrogation can be used to capture an image of the retina or other structures in the eye, or may be used to detect eye movement either generally or as part of diagnostic or user performance testing.

FIG. 6a shows an illustration of the palpebral surface of an eyepiece 100. A structure similar to that of FIG. 5 is shown, with electronics including a plurality of electrodes 102 sandwiched between an inner piece 104 and an outer piece 106. Six electrodes 102a, 102b, 102c, 102d, 102e and 102f are shown, but any suitable number may be used. The area spanned by the electrodes may vary widely. As will be readily understood, the above table showing combinations for two superior and two inferior electrodes on an eyepiece would be expanded with additional columns and many additional combinations for therapy output may be defined with six electrodes.

In some examples, the electrical components used to deliver electrical therapy via the electrodes may include a multi-channel topology. Separately addressable voltage and/or current sources may be used, having one source, two sources, or as many such sources as there are electrodes, if desired, or even with more sources than electrodes. Some sources may output current (current sources) or drain current (current sinks), while others may provide positive or negative voltages relative to system ground/reference. In some examples, there may be dedicated voltage or current circuits for each electrode while in other examples, a bank of voltage or current generating circuits may be coupled by an array of switches or a multiplexor to the output electrodes, allowing therapy generating circuits to be ganged together on a single output electrode or spread out across a number of electrodes.

Miniaturization of a neural stimulator has been taken to great lengths including providing communication, pulse output, power storage and/or control circuitry in implantable devices of just a few grams and cubic centimeters, such as shown in U.S. Pat. Nos. 5,193,540 and 8,612,002, the disclosures of which are incorporated herein by reference. Moreover, the provision of multiple channel outputs has been shown as well, including for example in U.S. Pat. Nos. 5,643,330 and 6,516,227, the disclosures of which are incorporated herein by reference. Each of these referenced patents provides designs and/or details that may be used in the present invention to miniaturize the device and /or electronics.

If an adhesive element is used, such as shown in FIG. 6b, the adhesive element 110 may include gaps or cutouts 112 within an adhesive region 114, to allow adhesion to the skin while also placing the electrodes 102 (FIG. 6a) in contact with the skin of the user. In an example, rather than gaps or cutouts 112, a replaceable adhesive element may have first regions of adhesive and second regions of a conductive hydrogel to facilitate conductive contact with the skin of the user. In a still further alternative, there may be no gaps or cutouts, and instead, the adhesive element may be conductive in general.

FIG. 7a shows an illustrative example in which a charging/control device 130 has a plug 132 for coupling to the protrusion 122 of an eyepiece 120. Illustratively, the protrusion may contain electronics for the eyepiece 120 or, alternatively, the protrusion may hold the port for receipt of the plug 132, with electronics elsewhere on or in the eyepiece 120. The plug 132 may be used to charge and/or program therapy or stimulation of the eyepiece 120. Coupling via the plug may also be useful to download stored data relating to usage of the eyepiece and/or stored therapy or diagnostic information. The plug 132 may take any suitable form such as USB, mini-USB, infrared or other optical coupling, or various alternatives known in the art; a proprietary connector may be used to prevent misuse if desired. The controller device may be a dedicated programmer, a smartphone, a tablet computing device, a laptop computer, or simply a charger. As noted, in other examples, the interface between an eyepiece and a charging or reprogramming device may be wireless instead.

While protrusion 122 is shown more or less in the center of the eyepiece 120, in an alternative construction, the protrusion may instead be placed on the perimeter of the eyepiece 120, as shown at 148. As with protrusion 122, the protrusion 148 may contain circuitry and electronic componentry of the device 120. A single eyepiece 120 may have multiple protrusions 122, 148 in some examples, while in other examples there may be only one protrusion 122, 148.

FIG. 7a also shows a case 140 for holding the eyepiece 120 when not in use. There may be one or more wells 142 for receiving individual eyepieces 120, and a well 146 for receiving the cord with plug 132, and a well 144 for receiving the charging/control device 130. In some examples, only wells 142 are included in the case 140.

FIG. 7b shows another example. Here, the eyepiece 150, which may have various features common with eyepieces shown above and below in the present disclosure, is shown with a protrusion 152 having electrical contacts 154 on the outside thereof. A case 156 is shown with a base 158 and a lid 162. The base and lid define a shell for the container, and one or the other may include a touchscreen, a viewing screen, one or more LED or other indicators, buttons, a keyboard, or other suitable user interface elements to provide a user interface that offers one or more of charging status, programmable parameter reports, device history or status, and, optionally, the capability for modifying stimulation parameters.

The base 158 and lid 162 may be separate pieces or may be hingedly attached together. The base 158 includes one or more wells 160 shaped to receive the palpebral portion of the eyepiece 150. The lid 162 includes corresponding wells 164 with sockets 166 for receiving the protrusion 152 of the eyepiece 150. Inside the sockets 166 are contacts (not shown) for making electrical contact with the contacts 154 of the eyepiece 150 protrusion 152.

The protrusion 152 and sockets 166 may have a shape, such as a triangle as shown (or any other suitable shape) to ensure that the user places the eyepiece appropriately to enable an electrical contact. Such electrical contact may in turn be used to recharge the eyepiece 150. The case 156 may be battery or plug-in operated. In an example, the case 156 may comprise its own power supply and rechargeable batteries and may be adapted for periodic recharging. The eyepiece 150 may be recharged as needed by placing the eyepiece 150 appropriately in a well 164, and the case 156 can be recharged weekly or monthly, for example, by plugging into a wall outlet. Such electrical connection may also be used to communicate with the memory and/or control circuitry of the eyepiece 150, allowing reprogramming and/or download of diagnostic, usage, therapy or other data. If desired, the outer surface of the case 156 may include a user interface to indicate to a user that charging is actually occurring and/or to allow the user to change programming settings if desired. If two eyepieces are coupled together with a nosepiece (such as in FIGS. 18-19, below), the various wells may be modified accordingly.

Figure 9:
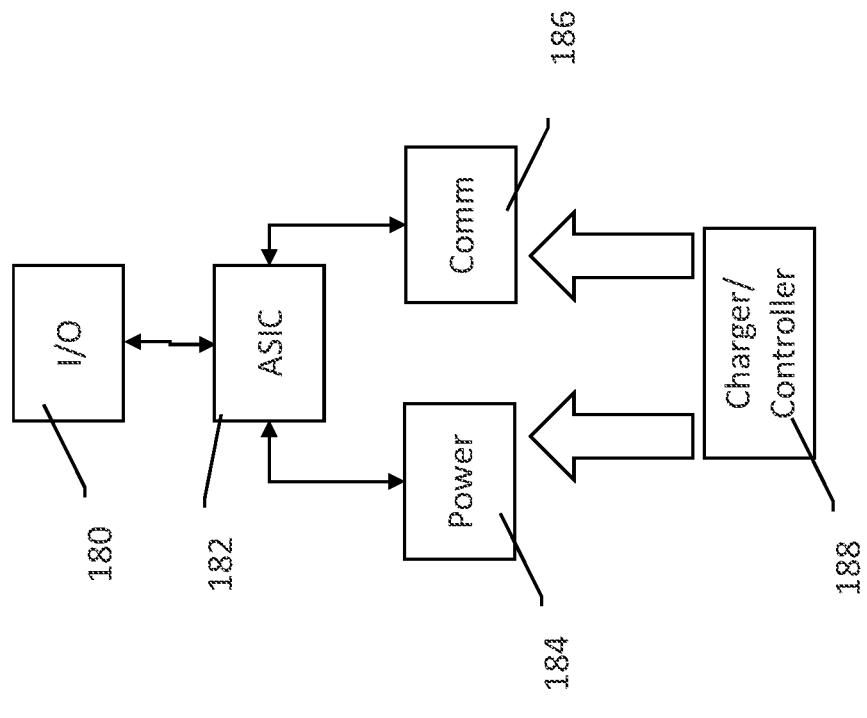
Figure 8:
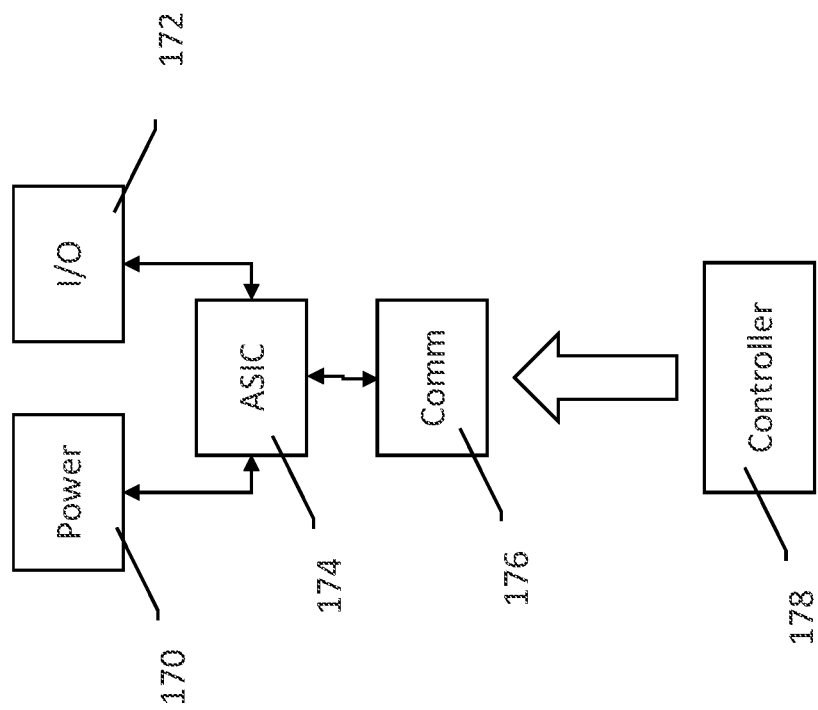

FIGS. 8-10 show illustrative electrical component architectures. In FIG. 8, a power block 170 is provided and can be a rechargeable or non-rechargeable battery. An application specific integrated circuit (ASIC) is included at 172 and couples the power 170 to input/output (I/O) 172, which may alternatively be integrated in the ASIC, if desired. The ASIC may include control circuitry, memory, and various operational circuits such as current or voltage sources, operational amplifiers, filtering circuitry, etc. as the skilled artisan will recognize may be used to control device operation. For example, the ASIC may comprise circuitry defining a state machine, or may include a microprocessor. The ASIC may include memory for storing instructions, diagnostic data, usage history, or any other suitable data to be retained or used. In other examples, an ASIC 174 may be omitted and replaced with discrete electronic componentry, a microprocessor or microcontroller with associated memory and any suitable electronic hardware. A field programmable gate array package may be used as well, if desired, to provide additional circuitry.

The I/O 172 can couple to the wires that attach to the electrodes. A set of switches, for example, may be included in I/O as well as buffering or protective circuits such as DC blocking capacitors. A communications block is shown at 176 and may be, for example, MedRadio telemetry block, an inductive telemetry circuit, or a Bluetooth™ circuit, such as a Bluetooth™ Low Energy (BLE) circuit, having an antenna and related circuitry (such as a crystal oscillator) for performing telemetry using RF energy. In this example, a controller 178 can be a programming device that provides a set of instructions executable on the ASIC, which may include or be implemented as a field programmable gate array or other field programmable element to deliver a planned therapy regimen. In other examples, therapy output may be commanded by the controller 178, such that the product itself stores no information about the desired therapy and simply receives commands to issue outputs of duration, amplitude, frequency, etc. set by controller 178. The programmer 178 may be a dedicated device or may be a multiuse device, such as a smartphone or tablet computer.

FIG. 9 shows another example, except in this case the charger/controller 188 provides both telemetry and power to the device. In this example, the I/O block 180 is configured to receive therapy output signals from the ASIC 182. The ASIC 182 receives both power 184 and communications 186 from a charger/controller 188. The components for each of 180, 182, and 186 may be similar to those of FIG. 8. In this example, the power receiving circuitry may include, for example, a rectifier and capacitor configured to receive electrical power from a receiving element, such as an inductive coil and/or an RF antenna, or a transducer such as a piezoelectric element or ultrasound or optical receiver, any of which may be powered by the charger/controller 188.

The signal that carries power may also carry data and/or commands from the charger/controller 188, and so there may be shared components between the power 184 and communications circuit 186. For example, if an RF signal is generated by the charger/controller 188, an antenna may be shared by the power and communication 184, 186 blocks, with the communication block 186 having demodulation circuitry configured to extract data from the carrier signal of the RF signal, while the power circuit captures the power from the carrier signal. Likewise, an inductive communication and power signal may be generated by the charger/controller 188. In other examples the charger/controller 188 may provide more than one signal, such as an inductive signal captured by an inductive coil in the power block 184 and an RF or optical signal received by the communication circuit 186. The communicated data or commands may, for example, set parameters for therapy delivery (amplitude, pulse width, shape, frequency, pattern, electrode selection, etc.), and the ASIC 182 can then cooperate with the I/O 180 and power block 184 to provide the commanded therapy to the user.

For this example, the system may omit a separate power storage element in the form of a rechargeable battery, and include instead a shorter term electrical storage element such as a relatively simple capacitor circuit, or capacitor block, as needed, to provide therapy only during a communication session with the charger/controller 188 or only for a limited period of time after the charger/controller 188 ceases to deliver a signal.

FIG. 10 shows another example. Here, the charger/controller 190 provides an output signal that is received by a transducer circuit 192, which directly feeds a signal to the I/O. The transducer circuit may directly convert received signals into output electrical signals, for example, by passing a received inductive, RF, optical, or mechanical signal (such as ultrasound) directly to the user through the I/O after conversion to electrical energy/current. The transducer may serve to condition the received power, such as by smoothing, rectifying, and/or limiting power passed through. The example shown in FIG. 10 may use principles similar to those used by an RFID chip, for example.

FIG. 11 shows an example of use of the system by a user 200. The user 200 is shown wearing an eyepiece 210 over the left eye, with the right eye 202 uncovered. A controller 220 communicates with the eyepiece 210, and may operate as in any of the various examples above, including those of FIGS. 9-11.

FIG. 12 shows another example. Here, the eyepiece 230, which may be similar to and/or have features of various eyepieces discussed above includes a temporal edge 234 and nasal edge 236, with a field region 239 therebetween. A protrusion 232 in this example may be used to house electronics of the system and/or useful for the user to place and/or remove the eyepiece 230 from the vicinity of the eye. In this example, the protrusion 232 is not central in the field region 239 of the device, which may be useful to reduce the obstruction in the visual field of the user that central placement may create. For example, if the eyepiece 230 has a clear or semi opaque portion to allow the user to see while wearing the eyepiece, moving the protrusion 232 off-center, as shown, may enhance the user's ability to see, as contrasted with a centrally located protrusion. In another example, the field region 239 may have a void to allow the user to see out, and the protrusion 232 can be placed on the periphery to leave the void unobstructed.

FIG. 12 also shows separate indifferent or remote electrode 238 that is tethered to the eyepiece 230 and may couple, as shown, to the protrusion 232. In an alternative, the remote electrode 238 may couple at the temporal edge 234, or elsewhere on the eyepiece 230. The remote electrode 238 may be used as anode or cathode, or ground/reference, relative to other electrodes of the system. The remote electrode 238 may be placed, for example and without limitation, on the temple, near the ear, on the front, back or side of the neck, in or on the nose or sinuses, on the shoulder or torso of the user, or on a limb. In this example, an adhesive or contact enhancement piece 242 is provided on a sheet of material, such as a sheet of plastic 240. As shown, there may be regions of conductive gel or opening/gaps 244 on the contact enhancement piece 242. In another example, rather than a sheet of material, the contact enhancement may be provided as precut pieces on a roll of double sided medical tape.

The contact enhancement piece 242 may be a replaceable element of the system. For example, a sheet of paper, waxed paper, or plastic (or other material) carrier may have a plurality of replaceable adhesive or contact enhancement pieces 242. The replaceable adhesive or contact enhancement pieces 242 may each have a removeable or peel-away structure on a first side thereof, while the second side is coupled to the sheet 240. A first of the plurality of replaceable adhesive or contact enhancement pieces 242 can be selected and the first or second side thereof applied to an eyepiece, remote electrode, or other part of the system that is intended to be fixed in position on a user. The other side of the selected adhesive or contact enhancement piece 242 is then exposed by removal of the peel-away structure and placed on user/user tissue. After one or several uses, the adhesive and/or conductive capability of the first replaceable adhesive or contact enhancement piece 242 may degrade and so the first replaceable adhesive or contact enhancement piece 242 can be discarded, and a next one of the replaceable adhesive or contact enhancement pieces 242 may be selected and put into use.

A protrusion may be omitted in some examples by using thin-film circuitry to provide various functions of the device. In some examples, such thin film circuitry may comprise a power receiving circuit (such as an antenna or inductor/coil) and the device may operate using a configuration as in FIG. 9 or 10. A charging apparatus for use therewith may be placed in any suitable position, such as on the head or neck of the user or in a garment.

Figure 13A:
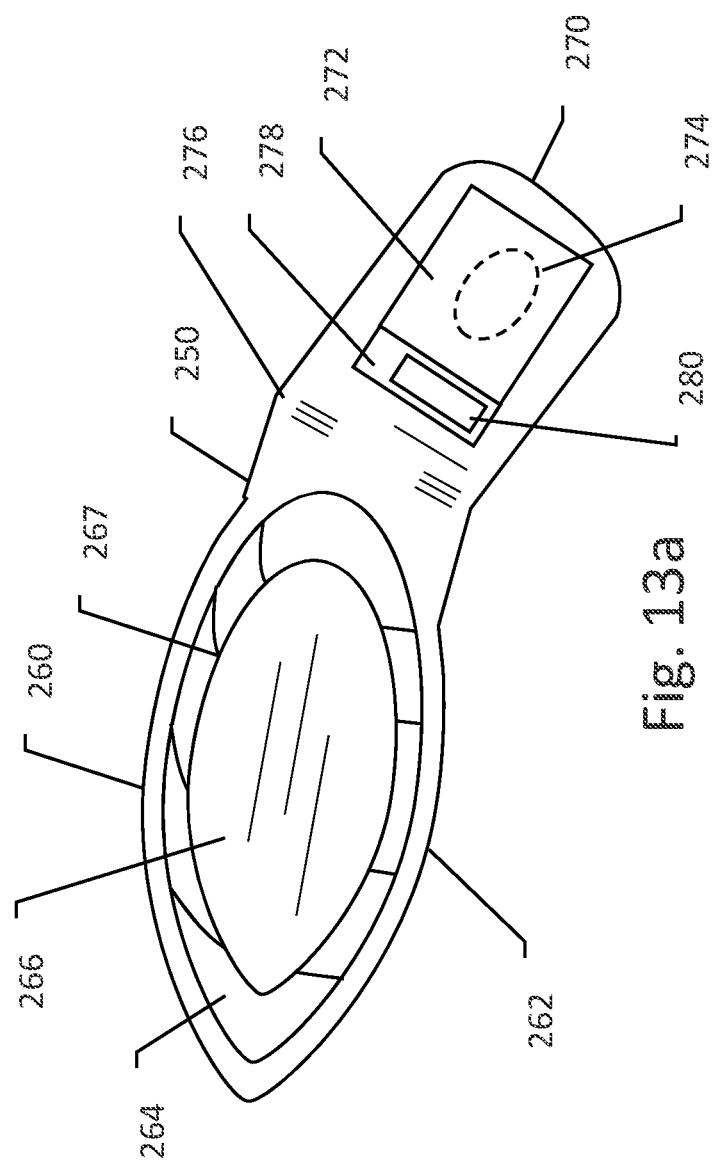

FIG. 13a shows another example. Here, an eyepiece is paired with a lateral extension that wraps around to the temple of the user. The device 250 has an eyepiece 260 and lateral extension 270; the lateral extension may also be referred to as a temporal portion or temporal region of a device. The device 250 includes a first region 262 that can include a flexible material adapted to contact user skin and, in some examples, to facilitate holding the device at a desired position by mechanically pressing against the bones around the eye or by adhering to the eyelid and/or other skin as needed. Adhesives suitable for adhering the eyepiece to the skin are known in the art and include, for example 3M 1509 Transparent Polyethylene Double Sided Medical tape.

The eyepiece 260 includes a field region 266 which may be a void or a solid material that is transparent or selectively transparent (such as by the use of a photochromic or electrochromic material). The field region 266 may be or include a lens made with reference to a user's corrective eyeglasses prescription, or may be adapted to receive a corrective lens therein. For example, the field region 266 may define an inner perimeter 267 sized and shaped to receive a corrective lens; for such purposes the inner perimeter 267 may be flexible to receive and hold a corrective lens by friction fit. Alternatively the field region 266 may be a single piece with or without vision correcting features.

The lateral extension 270 carries the electronics in an electronics block 272. Optionally, a remote electrode may be included as indicated in phantom at 274, for coupling to the temple as the lateral extension 270 wraps around the user's forehead to the temple. The lateral extension 270 may include a bending region 276 with a preset bend. Alternatively, there may be no preset bend, and the lateral extension 270 may include an adhesive piece or pieces to hold it in place on the temple. The adhesive piece or pieces may be included as well with examples that have a preset bend at region 276.

In the example shown, the electronics block 272 may be attached or plugged into a port 278. This may allow removal of the electronics block 272, which may serve a variety of purposes. In one example, the electronics block 272 may be removed and replaced once the (non-rechargeable) battery is depleted. In another example, the electronics block 272 is only partly removed, such as by removing a battery or battery holder, to allow the battery to be replaced once depleted. In another example, the electronics block 272 may be non-reprogrammable, and therefore may be removed and replaced to change a therapy program. In yet another example, the electronics block 272 may be removed to allow replacement of the rest of the device. In another example, the electronics block 272 may be removed and placed in a charger for recharging it, or placed in or coupled to a charger/programmer to facilitate a one or more of recharging, reprogramming and/or download of diagnostics or therapy history.

In each of the examples herein, the eyepiece may comprise a button, toggle, touch activated region, or other user-actuated switch 280 to allow a user to turn therapy on or off. Such a switch 280 may be provided, for example, on a protrusion for some of the above eyepieces as in, for example, FIGS. 1, 3, 5, 7a-7b, and 12, or elsewhere on such devices. A switch 280 may also be provided on the electronics block as shown in eyepieces as in FIGS. 13a-13c, and 14a-14d. A switch 280 may be provided elsewhere, if desired. In some examples, a temperature sensor may be used, or an impedance sensor, to automatically turn therapy on, or enable a switch 280 to allow turn-on of therapy, when the user's skin is contacted by the sensor or electrodes, indicating that the user is wearing the apparatus. In other examples, a user remote control may be used to turn therapy on and/or off, such as using a dedicated remote control in the form of a key FOB or other design, or by allowing a user to use an application operable on a smartphone or tablet, for example, or using any suitable device having communications capability to link to a therapy delivery apparatus. In some examples, the eyepiece may provide a visual indicator, such as an LED, on the external or palpebral side, to indicate whether and/or when the system is "On" and delivering therapy.

Particularly when therapy is configured to be imperceptible to the user, it may be useful to provide a non-therapy indicator or annunciator to the user. In some examples, the user may use a switch 280 or user remote control to turn therapy on and, to confirm the on state, a speaker, light, or other annunciator may be used to indicate that therapy has been turned on to the user. Such annunciation may again be used if therapy is turned off by the user, or when a therapy session is completed.

FIG. 13b is a top down view, showing that the device 250 includes eyepiece 260 with first region 262 adapted for tissue contact, and the field region 266 extends out and away from the eye, similar to swim goggles, for example. The electronics block 272 is shown with a raised profile that extends outward from the lateral extension. Optionally, in other examples the electronics block 272 may present a lower and/or smooth outer profile instead. As illustrated in FIG. 13c, the device may be adapted to lay more or less flat, allowing easy storage.

Figure 14A:
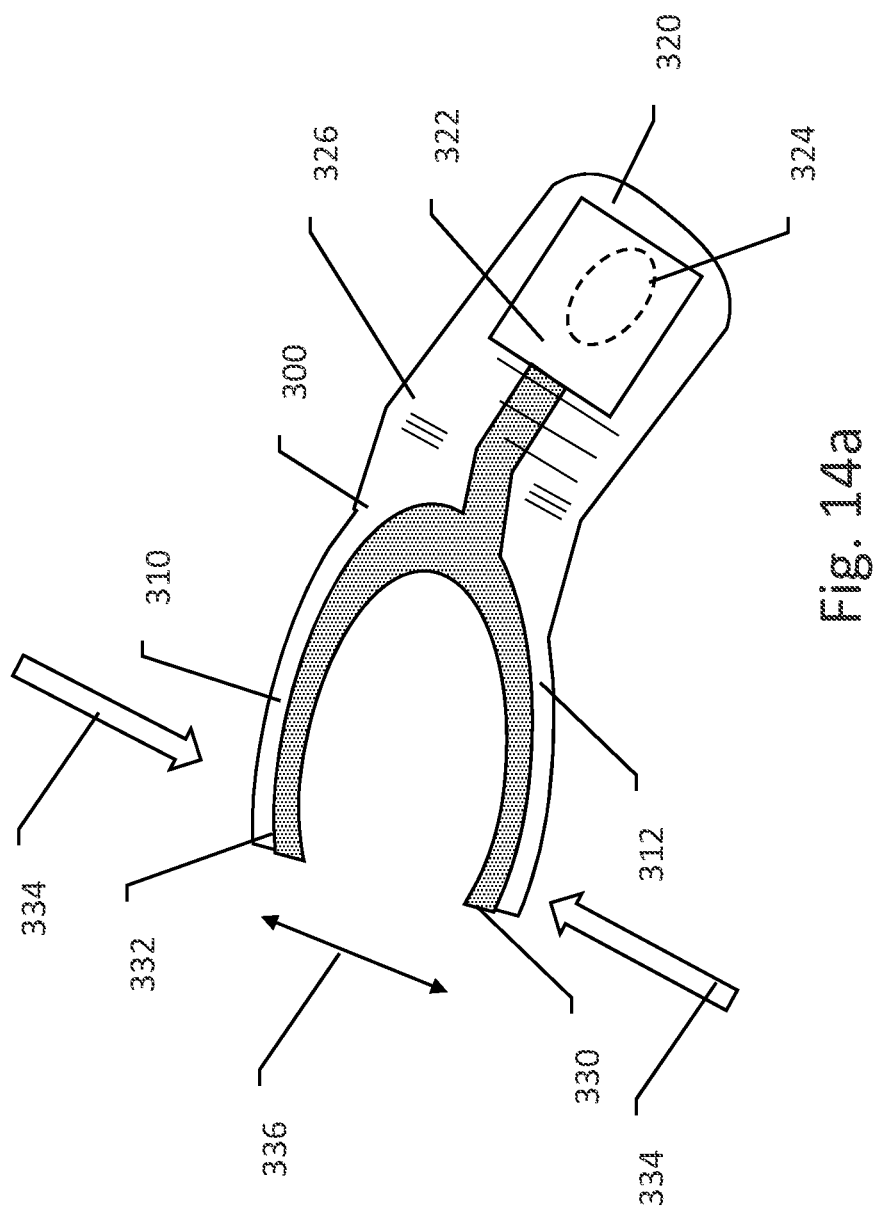

FIG. 14a shows another example. Here, the device 300 has a first portion or eyepiece 310 that partly surrounds the eye, but without fully covering the eye. This may allow the user to have full visibility while using the product. The eyepiece 310 comprises electrical connectors for coupling an electronics block 322 on the wrap around piece 320. In another example, a flex circuit may be provided as a single piece 312, which may be, for example, laser cut to a desired shape and size as shown. An optional temporal electrode, which may be a remote electrode used as described above, is shown at 324 in phantom. The eyepiece 310 may be described as having a first or inferior arm 330 and a second or superior arm 332 which define an open oval by not going the entire way around the eye. For placement, the inferior and superior arms 330, 332 maybe squeezed as shown by arrows 334, and then released to exert radial outward forces against the skin and bones around the eye in direction 336. By such action, the inferior and superior arms 330, 332 may provide mechanical fixation to the apparatus. The mechanical fixation may be aided by the use of an adhesive layer at the tissue interface, if desired and in accordance with various examples above.

FIG. 14b is a top down view, showing a use configuration of the device of FIG. 14a, with device 300 bending around the user's head with the eyepiece 310 and wrap around portion 320, with electronics 326 on the wrap around portion. As shown in FIG. 14c, omission of a lens or other covering for the whole eye may allow the product to have a generally flat configuration when not in use, making for easy storage and/or transport.

FIG. 14d shows another alternative. The device 350 is shaped to surround the temporal edge of the eye, an inferior or first arm 352 and a superior or second arm 354 that can be squeezed in a first direction 360 for placement about the eye of a user, yet are resilient enough to secure the apparatus in place about the eye of the user by pressing in direction 362. Electrodes may be placed about the apparatus as desired. Adhesive may be used in place of mechanical fixation or to augment mechanical fixation. In an alternative, the device is configured for placement on the nasal side of the eye, rather than the temporal side. The electronics 350 may be placed along one of the arms, such as on the inferior arm 352. Rather than flexible arms, the apparatus may instead have a flexible region at 358, or may have a hinge such as a spring loaded hinge located in region 358.

FIGS. 15a-15c show additional examples. Here, a device 400 has a lateral extension 410 adapted to be placed on the temple, connected to an eyepiece 412 by an intermediate portion 414. The eyepiece 412 include a bridge 420 carrying a plurality of arms 422 each having an electrode 424 at a tip thereof. Three arms 422 and electrodes 424 are shown on each of a superior and an inferior bridge in FIG. 15a; more or fewer arms and electrodes may be included. In an example, the lateral extension 410 may carry electronics of the system, and may also be adhered to the temple of a user to aid in holding position. Additionally or alternatively, mechanical placement may be performed by the user squeezing the bridges 420 together as shown at arrows 428 and placing the device in position, and then releasing the bridges, allowing an outward force along line 426 to be exerted against the eyelid and/or skin, bones and/or other tissue surrounding the eye. The user may close the eye during placement so that the eyelid can completely close and open after placement.

FIG. 15b is a partial view along line b-b illustrating that the arms 422 on the eyepiece 400 extend toward the palpebral surface to place the electrodes 424 in contact with the eyelid. In this example, the electronics for the system may again be carried largely on the lateral extension 410 or, alternatively, may be placed remotely. In addition, the lateral extension 410 may include an adhesive piece to hold the device in place on the user without requiring an additional strap or earpiece.

FIG. 15c shows another alternative design. Here, the lateral extension of FIGS. 15a-15b is omitted, and the eyepiece 430 comprises an inferior bridge 432 and a superior bridge 432' that are placed about the eye of the user, again by squeezing the eyepiece along the direction shown by arrows 442, and releasing once the position desired has been achieved, allowing the bridges 432, 432' to exert a radial outward force along line 440 to gently mechanically hold the product in place. In this example, rather than a separate lateral extension, the product may carry the electronics in block 438. In some examples, the bridges 432, 432' themselves may flex during placement, while in other examples, the place where the two bridges meet, more or less at block 438, may include a spring hinge that allows hinging under pressure applied in the direction of arrows 442 to compress the bridges 432, 432' together for placement.

FIGS. 16a-16b show still another example. Here, a device 450 again has a temporal region 460 connected to an eyepiece 470. The eyepiece 470 includes struts 472 that hold in place a pair of palpebral contact strips 474, which are longer strips rather than individual electrodes. One or more electrodes may be carried on each strip 474. FIG. 16b shows a partial section view, illustrating how the struts 472 carry the strips 474 to be pressed against the eyelids. In this example, the electronics for the system may again be carried largely on the lateral extension 460. Such electronics may include a power supply or, in some examples, power may be remotely supplied. In addition, the lateral extension 460 may include an adhesive piece to hold the device in place on the user without requiring an additional strap or earpiece. Squeezing the eyepiece along the direction of arrow 476 can compress the eyepiece for placement; when released, the eyepiece may exert a force in direction 478 against the eyelids and/or surrounding tissue to hold in place, similar to previous examples, with or without additional adhesive attachment.

For any of the examples herein, a remote power source may be provided around the neck of the user using examples as shown in U.S. patent application Ser. No. 16/697,689, titled HEAD WORN APPARATUSES FOR VISION THERAPY, the disclosure of which is incorporated herein by reference. Remote power may instead be worn on the head, on a garment, on the shoulder of a user, or any other suitable position.

FIG. 16c illustrates a further example, similar to FIGS. 16a-16b, but this time omitting the temporal region to wrap around to the temple. Instead, at the temporal edge of the eyepiece 480 is an electronics block 490. Again, the eyepiece 480 includes struts 482 that couple to and hold in place palpebral contact strips 484. Squeezing the eyepiece along directions 492 can compress the eyepiece for placement; when released, the eyepiece may exert a force in direction 494 against the eyelids and/or surrounding tissue to hold in place, similar to previous examples, with or without additional adhesive attachment. In another example, the electronics portion 490 may be moved to a superior or inferior location and the device may hinge or bend at the illustrated temporal or lateral edge of the eye. The device may be reversed as well such that the electronics 490 represents the nasal edge; again, a hinge or flex portion may be provided at the nasal edge if desired.

In still further examples, a shape memory material such as Nitinol™, or other known shape memory alloy/material, may be used. The two most prevalent shape-memory alloys are copper-aluminum-nickel, and nickel-titanium (NiTi) alloys, additional compositions with shape memory characteristics can be had with alloys of zinc, copper, gold and iron, as well as iron or copper based alloys such as Fe—Mn—Si, Cu—Zn—Al and Cu—Al—Ni. Because nitinol contains nickel, which may cause a biological reaction in some users (i.e., nickel allergy), the material may be coated with an inert layer of biocompatible polymer or an extra coating of a biocompatible metal. In one example, a shape memory material is selected such that, when not on the user's body, the material is elastic, and when placed in contact with the user's skin, the shape memory material transitions to its "memory" shape and serves to apply radial forces to mechanically hold a device in place about the eye. As will be understood, any of the eyepieces disclosed herein having two or more shape configurations provided by elastic or hinged materials for compression and release can also be provided by shape memory materials such as Nitinol.

Figure 17:
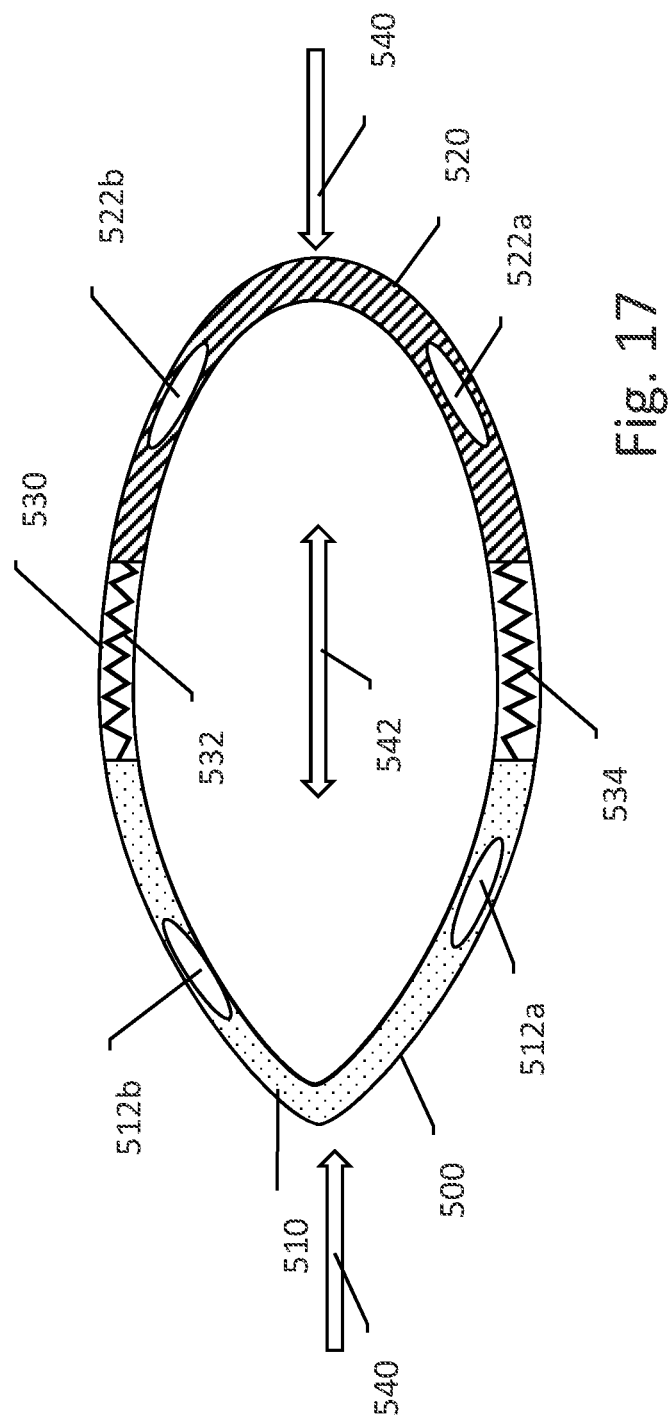

FIG. 17 is a section view of another illustrative device. The device is shown as an eyepiece having a nasal section 510 and a temporal section 520 with a coupling section 530 therebetween. The nasal section 510 may include one or more electrodes 512a, 512b, and the temporal section 520 may also include one or more electrodes 522a, 522b. The coupling section 530 houses one or more compression members 532, 534, which may be, for example, springs (such as a coiled spring or serpentine ribbon), a compressible foam or sponge, a compressible cylinder housing a fluid (such as air, water, etc.), or a shape memory alloy. To receive therapy, the user compresses the eyepiece as shown by arrows 540, then places the eyepiece as desired and, upon release, the one or more compression members 532, 534 exert an outward force along line 542 to provide mechanical fixation of the eyepiece in the vicinity of the eye.

If using a shape memory alloy, such as Nitinol™ or other shape memory alloy, in some examples the alloy can be selected and conditioned to have an austenite temperature in the range of about 80 to 100 degrees Fahrenheit, more preferably in the range of about 85 to 95 degrees Fahrenheit. With such a temperature range, the user can reshape the device prior to placement in the eye socket region while the alloy is quite shapeable. On placement in the region of the eye socket, the alloy will be warmed with proximity to the user's tissue and cross its austenite threshold and create spring tension to hold the eyepiece in position.

As with other examples, adhesive fixation may be used as well. Other arrangements to the electrodes are contemplated, including fewer or more electrodes on the nasal or temporal sections 510, 520, and or including one or more electrodes on the coupling section 530. In other examples, the compression members 532, 534 may be operable in the superior-inferior direction, rather than in a medial-lateral or nasal-temporal direction.

FIG. 18 shows an example of goggles having a first eyepiece 600 and a second eyepiece 610 coupled together by a nosepiece 620. The example shows the inclusion of protrusions 602, 612 for housing electronics, including for example control circuitry and power supply, which may encompass any of the designs shown above in FIGS. 9-11. In some examples, two electrically independent and complete systems may be provided in one set of goggles, with each eyepiece 600, 610 independently operable. In other examples, a single set of electronics may be provided to control both eyepieces 600, 610. In another example, a shared reference voltage connection may be provided and therapy of two independently operable eyepieces 600, 610 may be coordinated with one another allowing, for example, therapy delivery using an electrode on one eyepiece as an opposing pole to an electrode on the other eyepiece, as well as other suitable combinations. U.S. Pat. No. 7,251,528 to Harold, U.S. patent application Ser. No. 16/589,383, titled SYSTEM AND METHODS FOR CONTROLLED ELECTRICAL MODULATION FOR VISION THERAPY, and Ser. No. 16/697,689, titled HEAD WORN APPARATUSES FOR VISION THERAPY, are each incorporated herein by reference as illustrating additional example waveforms and structures, as well as therapy output configurations that can use first and second eyepieces cooperatively to deliver therapy.

The system as shown in FIG. 18 may be used with a remote return electrode as well. Such a configuration would allow the delivery of therapy across a range of target depths in the rostral portion of the user's head as explained below.

FIG. 19 shows another example. Here, a therapy apparatus comprises a first eyepiece 650 and a second eyepiece 660 coupled together by a nosepiece 670. The nosepiece 670 may carry electronics (which may be as described elsewhere in the present disclosure) for the system and, optionally, may couple to a remote electrode 680 for placement for example and without limitation, on the temple, near the ear, on the front, back or side of the neck, in or on the nose or sinuses, on the shoulder or torso of the user, or on a limb. Eyepiece 650 comprises a plurality of electrodes including superior electrodes 654, 656 and inferior electrode 652, and eyepiece 660 comprises a plurality of electrodes including superior electrodes 664, 666 and inferior electrode 662. The eyepieces 650, 660 may have flexible superior and inferior arms that provide mechanical fixation as described above relative to FIGS. 14a-14d, 15a-15c, and/or 16a-16c, for example.

A range of therapy and/or diagnostic depths may be defined. For example, using electrodes 652, 654, 656 on a single eyepiece 650 for therapy output may target a structure toward the anterior of one of the user's eyes, such as the iris and/or trabeculae. Using electrodes on each eyepiece 600, 610 may target a structure more deeply positioned in the user's eye, such as the retina or lens, or may target a structure medial to the eyes such as the nasolacrimal ducts and/or canaliculi. Using electrodes on one or more of the eyepieces 600, 610 with a remote electrode may target still deeper structures such as the optic nerve. For diagnostic purposes, it may be useful to sense impedances between electrode pairs on a single eyepiece to determine tissue interface characteristics, for example, while a signal measured between one or more electrodes 652, 654, 656 on one eyepiece 660 and one or more electrodes 662, 664, 666 on the other eyepiece 660 may be useful to detect phosphenes occurring in response to therapy outputs, or to sense physiological changes in the eye. Other therapy combinations and diagnostic uses may be implemented as well, for these or other targets or diagnostic measurable; those noted are merely illustrative.

In the above discussion, in examples that include a remote electrode such as 680, an alternative approach to the power supply may be to place a battery or other source of power on the remote electrode 680, which is physically coupled to the rest of the electronics by wire connection. Such an approach may be implemented in any of the above examples. If a rechargeable battery is used, disconnecting the remote electrode and plugging it into a recharge module can allow replenishment of the power source. If a non-rechargeable battery is used, the battery may be removed from the remote electrode 680 and discarded when spent, or, alternatively, the remote electrode 680 and battery may be packaged together and both discarded when the battery is spent. Placing the battery on the remote electrode may allow low-cost standard batteries (such as alkaline batteries) to be used, as the mass of the battery is carried remotely from the eyepiece.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A wearable therapy apparatus for placement about an eye of a user comprising:
   a perimeter region including a tissue interface having at least one electrode thereon, the perimeter region having a superior edge, and an inferior edge and at least one electrode, the perimeter region sized and shaped for placement about the eye of the user with the superior edge superior to the eye and the inferior edge inferior to the eye;
   a field region defined within the perimeter region; and
   an electronics module electrically coupled to the at least one electrode, the electronics module adapted to deliver electrical energy to the user through the at least one electrode, wherein the electronics module is housed in a receptacle on one of the perimeter region or the field region.

2. The wearable therapy apparatus of claim 1 wherein the electronics module comprises a rechargeable or replaceable battery coupled to a pulse generator circuit adapted to generate output pulses, the pulse generator circuit having at least one output coupled to the at least one electrode, and a control circuit configured to determine parameters for the output pulses of the pulse generator.

3. The wearable therapy apparatus of claim 2 wherein:
   the at least one electrode includes at least two electrodes; and
   the control circuit is configured to use each of a pre-therapy test mode and a therapy mode, the pre-therapy test mode operable to issue electrical signals from the pulse generator circuit to the at least two electrodes while monitoring current flow to confirm electrical contact of the at least two electrodes to skin of the user.

4. The wearable therapy apparatus of claim 2 wherein:
   the at least one electrode includes at least three electrodes; and
   the control circuit is configured to use each of a pre-therapy test mode and a therapy mode, the pre-therapy test mode operable to issue electrical signals from the pulse generator circuit to a subset of the at least three electrodes while monitoring electrical field at an electrode that is not part of the subset to confirm electrical contact of the perimeter region to skin of the user.

5. The wearable therapy apparatus of claim 2 further comprising a temperature sensor coupled to the control circuit, wherein the control circuit is configured to prevent activation of the electronics module when the wearable therapy apparatus is not on a user's body by using the temperature sensor to sense body temperature.

6. The wearable therapy apparatus of claim 2 further comprising temperature sensor coupled to the control circuit, wherein the control circuit is configured to activate stimulus by the electronics module when the wearable therapy apparatus is on a user's body by using the temperature sensor to sense body temperature.

7. The wearable therapy apparatus of claim 1 wherein the electronics module comprises a wireless communication circuit for receiving commands including at least a command to initiate therapy.

8. The wearable therapy apparatus of claim 1 wherein the perimeter region is flexible to allow compression thereof in a superior-inferior direction prior to placement about the eye of a user, such that release of the compression provides a mechanical force to the tissue surrounding the user's eye aiding in fixation in a desired position.

9. The wearable therapy apparatus of claim 1 wherein the perimeter region comprises a superior arm and an inferior arm, and at least one of the superior arm and inferior arm is flexible to allow compression thereof in a superior-inferior direction prior to placement about the eye of a user, such that release of the compression provide a mechanical force to the tissue surrounding the user's eye, aiding in fixation in a desired position.

10. The wearable therapy apparatus of claim 1 wherein the field region forms a void, through which the user can see when the wearable therapy apparatus is worn.

11. The wearable therapy apparatus of claim 1 wherein the field region is closed and is formed of a transparent or semi-transparent material.

12. The wearable therapy apparatus of claim 1, wherein the perimeter region and field region make up a first eyepiece, further comprising a nosepiece and a second eyepiece coupled to the first eyepiece by the nosepiece, the second eyepiece having at least a second electrode, wherein the electronics module is electrically coupled to each of the first and second electrodes.

13. The wearable therapy apparatus of claim 1 further comprising a remote electrode coupled by a wire to the wearable therapy apparatus.

14. The wearable therapy apparatus of claim 1 wherein the electronics module comprises external contacts adapted to receive power from a storage case having corresponding contacts for recharging purposes.

15. A system comprising a wearable therapy apparatus as in claim 14 and a storage case having at least one well with a slot therein, the well being shaped and sized to receive the wearable therapy apparatus with the electronics module inserted into the slot, wherein the slot contains corresponding contacts, and the storage case comprises a user interface for allowing a user to determine charge status the electronic module rechargeable battery and/or to set or modify stimulus settings of the electronics module.

16. The wearable therapy apparatus of claim 1 wherein the wearable therapy apparatus has a mass in the range of about 5 to about 25 grams.

17. The wearable therapy apparatus of claim 1 wherein the electronics module is configured to sense impedance between the electrodes and to use sensed impedance to determine whether the wearable therapy apparatus is being worn by a user and, if so, to automatically deliver therapy.

18. The wearable therapy apparatus of claim 1 wherein the electronics module is configured to sense impedance between the electrodes and to use sensed impedance to determine whether the wearable therapy apparatus is being worn by a user and, if not, to automatically disable therapy.

19. A method of delivering energy to tissue to address a condition of the eye, the method comprising:
   providing a wearable therapy apparatus adapted for placement about the eye of a user;
   the wearable therapy apparatus determining whether it has been placed about the eye of a user; and
   the wearable therapy apparatus, after determining it has been placed about the eye of the user, issuing electrical energy therefrom;
   wherein the wearable therapy apparatus comprises:
   a perimeter region including a tissue interface having at least one electrode, the perimeter region having a superior edge, and an inferior edge and at least one electrode, the perimeter region sized and shaped for placement about the eye of the user with the superior edge superior to the eye and the inferior edge inferior to the eye;
   a field region defined within the perimeter region; and
   an electronics module electrically coupled to the at least one electrode, the electronics module adapted to deliver electrical energy to the user through the at least one electrode, wherein the electronics module is housed in a receptacle on one of the perimeter region or the field region.

20. The method of claim 19, wherein the at least one electrode on the perimeter region of the wearable therapy apparatus comprises a first electrode and a second electrode, and the step of the wearable therapy apparatus determining whether it has been placed about the eye of the user comprises the wearable therapy apparatus testing impedance between the first and second electrodes and comparing the tested impedance to at least one threshold to determine whether the first and second electrodes have been placed in contact with patient skin.

* * * * *